US00RE41807E

(19) United States
(12) Reissued Patent
Yokoi et al.

(10) Patent Number: US RE41,807 E
(45) Date of Reissued Patent: Oct. 5, 2010

(54) CAPSULE ENDOSCOPE

(75) Inventors: Takeshi Yokoi, Hino (JP); Akira Hasegawa, Musashino (JP); Shinya Matsumoto, Machida (JP); Takayuki Suzuki, Hachioji (JP); Hidetake Segawa, Hachioji (JP); Hironobu Takizawa, Hachioji (JP)

(73) Assignee: Olympus Corporation, Tokyo (JP)

(21) Appl. No.: 11/819,756
(22) Filed: Jun. 28, 2007

Related U.S. Patent Documents

Reissue of:
(64) Patent No.: 6,918,872
Issued: Jul. 19, 2005
Appl. No.: 10/378,622
Filed: Mar. 5, 2003

(30) Foreign Application Priority Data

Mar. 8, 2002 (JP) ..... 2002-064016

(51) Int. Cl.
*A61B 1/05* (2006.01)
*A61B 1/06* (2006.01)

(52) U.S. Cl. ..... 600/129; 600/130; 600/160; 600/179; 600/177

(58) Field of Classification Search ..... 600/109, 600/160, 129, 130, 176–181; 348/65, 68; 362/800
See application file for complete search history.

(56) References Cited

U.S. PATENT DOCUMENTS

| | | | | | |
|---|---|---|---|---|---|
| 4,278,077 | A | | 7/1981 | Mizumoto | |
| 4,856,880 | A | * | 8/1989 | Ohshita | 359/753 |
| 5,604,531 | A | | 2/1997 | Iddan et al. | |
| 5,681,260 | A | * | 10/1997 | Ueda et al. | 600/114 |
| 6,934,093 | B2 | * | 8/2005 | Kislev et al. | 359/708 |
| 6,939,292 | B2 | * | 9/2005 | Mizuno | 600/118 |
| 6,951,536 | B2 | * | 10/2005 | Yokoi et al. | 600/128 |
| 7,009,634 | B2 | | 3/2006 | Iddan et al. | |
| 7,433,133 | B2 | * | 10/2008 | Kislev et al. | 359/708 |
| 2001/0007051 | A1 | | 7/2001 | Nakashima | |
| 2002/0109774 | A1 | * | 8/2002 | Meron et al. | 348/74 |
| 2003/0020810 | A1 | | 1/2003 | Takizawa et al. | |
| 2003/0028078 | A1 | * | 2/2003 | Glukhovsky | 600/109 |
| 2003/0125788 | A1 | * | 7/2003 | Long | 607/133 |
| 2003/0130562 | A1 | | 7/2003 | Barbato et al. | |
| 2003/0171648 | A1 | | 9/2003 | Yokoi et al. | |
| 2003/0171649 | A1 | | 9/2003 | Yokoi et al. | |
| 2008/0200757 | A1 | * | 8/2008 | Glukhovsky et al. | 600/109 |

FOREIGN PATENT DOCUMENTS

| | | |
|---|---|---|
| JP | H04-109927 | 4/1992 |
| JP | H07-159702 | 6/1995 |
| JP | H11-192207 | 7/1999 |
| JP | 2000-037345 | 2/2000 |
| JP | 2001-87217 | 4/2001 |
| JP | 2001-91860 | 4/2001 |
| JP | 2001-091860 | 4/2001 |
| JP | 2001-290086 | 10/2001 |
| JP | 2001-346752 | 12/2001 |
| WO | WO 00/76391 A1 | 12/2000 |
| WO | 01/65804 | 9/2001 |

* cited by examiner

*Primary Examiner*—John P Leubecker
(74) *Attorney, Agent, or Firm*—Arnold International; Bruce Y. Arnold

(57) ABSTRACT

A capsule endoscope is disclosed that includes means for illuminating an object, means for imaging the object, and a transparent cover having a center of curvature. The transparent cover covers the illumination means and the imaging means, and the imaging means includes an objective optical system and an image detecting element. The illumination means is positioned relative to the image detecting element, as viewed axially from the object side of the capsule endoscope, so that an area that is symmetrically positioned about the optical axis of the objective optical system from a light emitting area of the illumination means overlaps an area of the image detecting element, but does not overlap any areas of the image detecting element that are used for image detection.

23 Claims, 13 Drawing Sheets

CAPSULE ENDOSCOPE

Matter enclosed in heavy brackets [ ] appears in the original patent but forms no part of this reissue specification; matter printed in italics indicates the additions made by reissue.

CROSS REFERENCE TO RELATED APPLICATION

This application claims the benefit of foreign priority from Japanese Patent Application No. 2002-064016, filed Mar. 8, 2002, the contents of which are hereby incorporated by reference.

BACKGROUND OF THE INVENTION

Endoscopes have recently come into extensive use in the medical and industrial fields. Recent medical endoscopes do not have an insertion member and there is no longer an insertion process. These are medical endoscopes are encapsulated within a capsule, which a patient can swallow. This eliminates the pain associated with insertion of prior art endoscopes that have an insertion member. Examples of capsule endoscopes include, for instance, those disclosed in the Japanese Laid-Open Patent Application 2001-91860 and the patent publication PCT WO 00/76 391 A1.

The prior art capsule endoscope disclosed in Japanese Laid-Open Patent Application 2001-91860 is provided with an objective lens and an illumination means consisting of light emitting diodes symmetrically located in relation to the objective lens within a nearly semi-spherical transparent cover. Part of the object is illuminated by the light emitting diodes and imaged by the objective lens onto an image sensor for observation. The prior art capsule endoscope disclosed in patent publication PCT WO 00/76 391 A1 includes a single, oval dome, optical window. An illumination element and a receiving element are positioned above or in contact with the focal curve plane of the oval dome. Plural illumination elements are positioned on the focal curve so that light from the illumination elements returns to some other point on the focal curve when a portion of the illumination light is reflected by the inner and outer surfaces of the window. Therefore, the receiving element is positioned somewhere other than on the focal curve in order to prevent light that is reflected at the interfaces of the oval dome surface from entering the receiving element, thereby preventing flare and ghosting that adversely affect the proper detecting of images.

The prior art capsule endoscope disclosed in Japanese Laid-Open Patent Application 2001-91860 does not describe a means to prevent or reduce flare and ghosting caused by a portion of the illumination light from the illumination means entering the objective lens after it has been reflected at air interfaces of the transparent cover. The prior art capsule endoscope disclosed in patent publication PCT WO 00/76 391 A1 uses an oval dome, transparent cover for the illumination and observation window, which is more costly to produce than a semi-spherical transparent cover. Furthermore, plural illumination elements are positioned on the focal curve. Since each element should be adjusted in position, this design requires additional labor.

When the illumination elements are light emitting elements (LEDs), the illuminating elements have a non-insignificant size. Therefore, in order to position the LEDs on the focal curve, the focal curve must be sufficient in length to accommodate the area in which the LEDs are to be positioned. This causes the size of the oval dome to become larger, which disadvantageously requires that the capsule be larger. However, increasing the size of the capsule is undesirable because it becomes difficult, even painful, to swallow such an encapsulated endoscope. Thus, the advantage of using a capsule endoscope is lost. Accordingly, the arrangement of the illumination means and the image detecting element within a capsule must be designed in a manner whereby the capsule can be made as compact as possible.

BRIEF SUMMARY OF THE INVENTION

The present invention relates to a capsule endoscope that is swallowed in order to examine interior regions of a living body. More particularly, the present invention provides a small-sized capsule endoscope having a transparent cover that is easy and inexpensive to manufacture, and which makes it difficult for undesirable light from the illumination means to enter the objective optical system.

BRIEF DESCRIPTION OF THE DRAWINGS

The invention will become more fully understood from the detailed description given below and the accompanying drawings, which are given by way of illustration only and thus are not limitative of the present invention, wherein.

DETAILED DESCRIPTION

The capsule endoscope of the present invention employs a transparent, dome-shaped cover, the inner surface of which has a center of curvature. Within the transparent cover there are provided a lighting means for illuminating an object outside the transparent cover and an imaging means which includes an objective optical system and an image detecting element that captures image data of an image formed by the objective optical system. The objective optical system may be arranged so that its optical axis lies on the center of curvature of the inner surface of the transparent dome.

When observing the internal wall of a lumen of a living body, the view field of interest is often at the periphery of the visual field. A transparent cover that is formed of a curved surface is installed in front of the imaging means, and the transparent cover is sealed to the capsule body. In such a case, the lumen-shaped internal part of interest at the periphery of the visual field is so near to the illumination means that over-exposure often occurs at the periphery of the visual field. More specifically, the capsule endoscope is constructed such that, when viewing the capsule endoscope from the object side, the positional relationship between the illumination means and the imaging means is determined so that an area that is symmetrical about the optical axis to the illumination means overlaps onto areas other than image-capturing areas of the image detecting element. In one case, a part of an image detecting area of the image detecting device is covered by an opaque member and the area that is symmetrical about the optical axis to the illumination means overlaps the covered area. In another case, a part of the image detecting area of the image detecting element is electrically masked so as to make the masked area inoperative and the area that is symmetrical about the optical axis to the illumination means overlaps the electrically masked area. Here, the word "inoperative" includes either that the pixels within an electrically masked area produce no electrical signal, or that they produce electrical signals which are not used to construct the image to be observed. In still another case, the area that is symmetrical about the optical axis to the illumination means overlaps the area outside the image detecting area. In either case, the area that is symmetrical about the optical axis to the illumination means overlaps an area of the image detecting element but does not overlap any area of the image detecting element that is used for picture image detection. Therefore, even when an illuminating beam is reflected by the internal surface of the transparent cover, such unwanted light will not contribute to the captured image, since it will not be incident onto active areas of the image detecting device.

Figure 15:
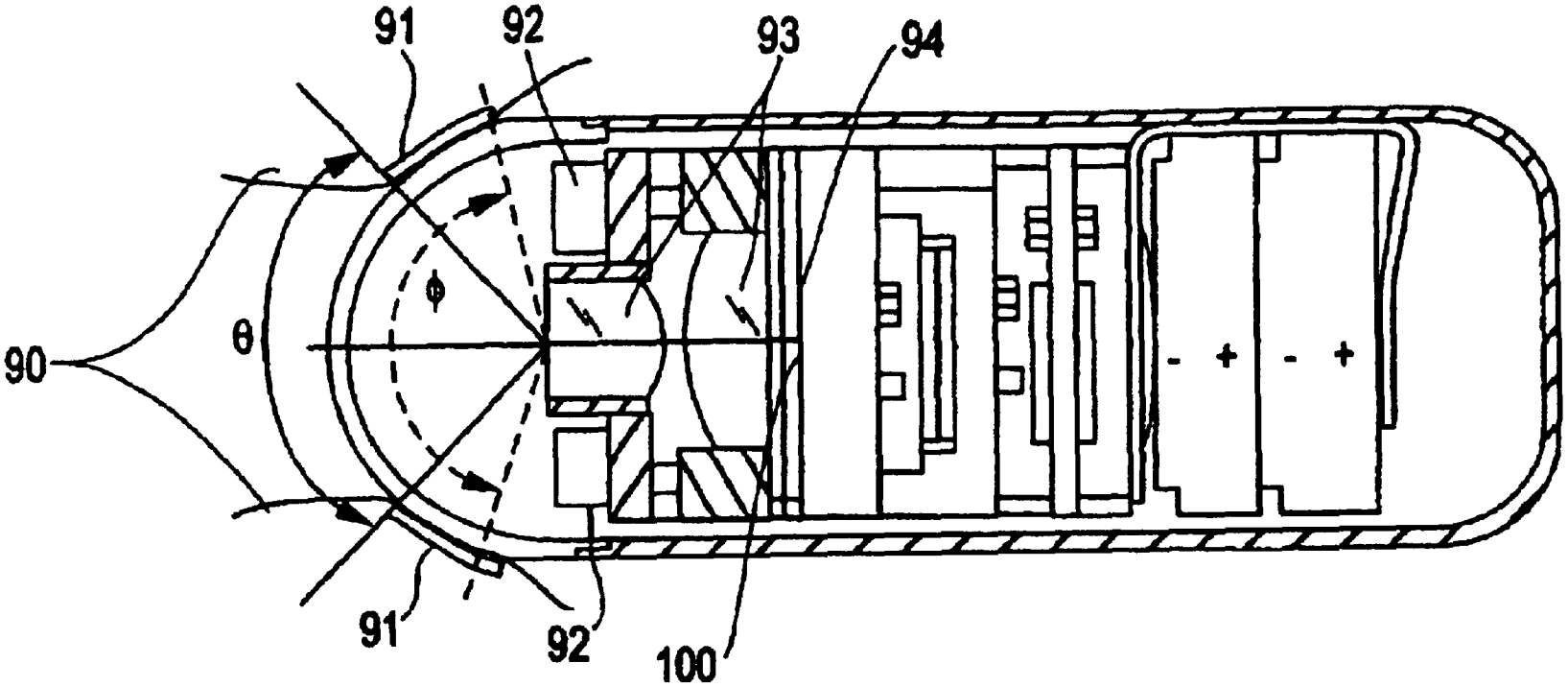
FIG. 15 is a cross-sectional view illustrating a capsule endoscope of the present invention moving within a lumen-shaped part of a living body.

FIG. 15 is a cross-sectional view illustrating the state of a capsule endoscope at the time of performing observations while moving within a small-diameter, lumen-shaped part within a living body. About 80% of the length of the human digestive tract (i.e., the usual observation path for a capsule endoscope) is within the intestine, which has a small diameter. The lumen-shaped internal part 90 has a portion 91 that lies immediately adjacent to the transparent window, and this portion (which is of primary interest) tends to become over-exposed by the illumination means 92. In a capsule endoscope having a transparent cover with a radius of curvature of about 5 mm, the over-exposed portion 91 of the object lies in a range that is centered about 3 mm from the illumination means 92. In this FIG. 93 is the objective optical system, 94 is the image detecting element, and 100 is the image plane.

Figure 16A:
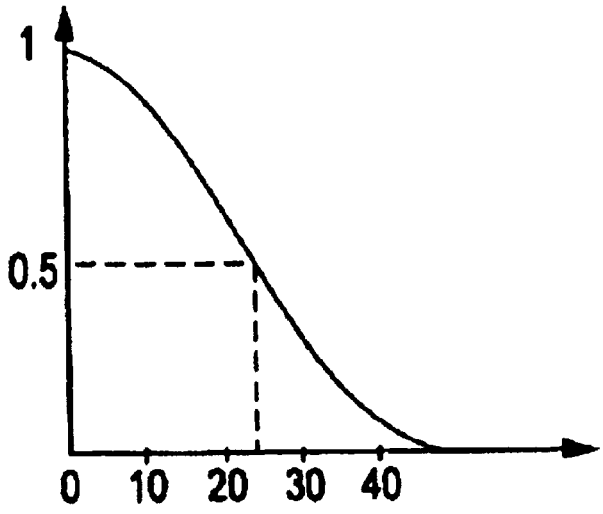
FIGS. 16(A) and 16(B) show two different light flux distributions, with FIG. 16(A) being the light flux distribution of a beam emitted from an LED such that the half-beam angle, as measured at the 50% of peak intensity points, is 25°, and with FIG. 16(B) being the light flux distribution of a beam emitted from an LED having a diffusion means such that the half-beam angle, as measured at the 50% of peak intensity points is larger, in this case 35°.
Figure 16B:
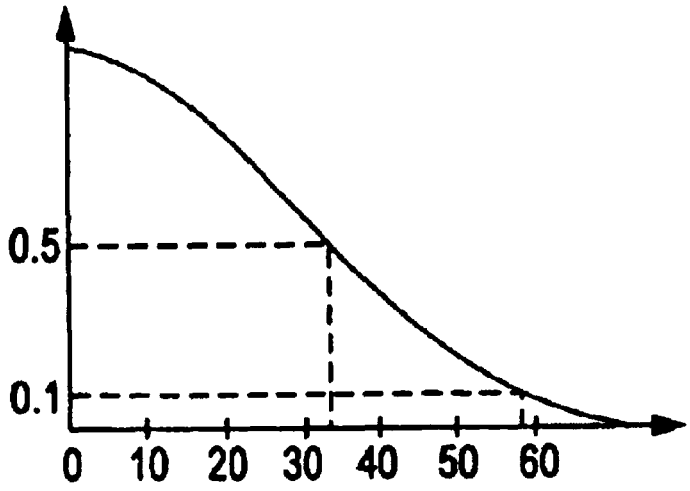

An LED is usually used as the illumination means. With Such an illumination means, there is a region that contributes particularly strongly to the illumination at the irradiated plane. Generally speaking, an LED's light flux output has a Gaussian distribution, with about 75% of the total light that is output being concentrated within an angular range, as measured from the optical axis of the LED, where the intensity ratio exceeds 0.5. This light strongly influences the illumination distribution at the irradiated plane. As shown in FIG. 16(A), light emitted from an LED has a flux distribution with a strong directivity, with the beam width (as measured on the X-axis) where the normalized intensity ratio (measured on the Y-axis) exceeds 0.5 being approximately 25°. Light rays emitted outside this beam width do not have a large effect on the illumination distribution at the irradiated plane. When using an LED having an improved flux distribution property as shown in FIG. 16(B), wherein a diffusion function is provided by a light diffuser positioned immediately in front of the LED, the beam width (as measured on the X-axis) where the normalized intensity ratio (measured on the Y-axis) exceeds 0.5 is about 35°. The latter case is preferred for use as the illumination means of a capsule endoscope. At Such time, if the light emitting plane of the LED is a circle having the radius r, the radius r is enlarged by a factor of approximately 2 to 3.5 when projected to a plane 3 mm ahead of the light emitting plane of the LED.

The image-formation relationship at the time of passing through an objective optical system 93 will now be described. An over-exposed portion 91 is an area that extends outside the visual field angle θ, and in this region photographic objects are reduced in size and form an image at a 'symmetrical area' on the image plane 100 that is on the opposite side of the optical axis of the objective optical system 93. The magnification of the objective optical system of a capsule endoscope for an object that is adjacent the transparent cover is in the range from about 0.25 to 0.5. On the other hand, the range where the objective optical system 93 is able to actually form an image on the image plane will be larger than the visual field angle θ as shown in FIG. 15. Accordingly, in the objective optical system of a capsule endoscope, the arrangement relationship between the objective optical system and the image detecting element is set so that an image-forming area from the excessive luminous flux outside the visual field angle θ is incident on an area of the image detecting element that is not used for image detection. Or, alternatively to such an arrangement, the range of the visual field angle θ may instead be determined by electrically masking the image-formation area outside the visual field angle θ at the time of picture image processing.

Therefore, the positional relationship between the illumination means and the imaging means when these components lie on opposite sides of the optical axis as viewed from the front of the capsule endoscope must be determined appropriately for a small-scale capsule endoscope in order to provide a visual field as large as possible and to provide a proper brightness so that over-exposure of an object within the visual field does not occur.

As described above, when using an LED with a light diffuser as the illumination means, the light emitting area of the LED is enlarged approximately 2 to 3.5 times when the emitted light is projected to a plane about 3 mm in front of the LED, and an object at this distance is then imaged by the objective optical system onto the image plane. The light emitting plane of the diffuser is imaged by the objective optical system with a magnification of approximately 0.9 to 1.0 because the magnification of the objective optical system in relation to an adjacent object is approximately 0.25 to 0.5. The position of the image is symmetrically located about the optical axis opposite the LED. This implies that an area on the image-detecting surface that is symmetric about the optical axis to the light emitting area of the LED with diffuser, when viewing the capsule endoscope axially from the object side, nearly matches the light emitting area of the LED with diffuser.

From the above description, if an area at the image plane that overlaps with an area that is symmetrical to the illumination means is made to be an area not used for imaging, the over-exposed portion can be avoided from being made into a picture image. In this manner, the high luminescent intensity of the illumination means can be avoided from degrading an image of an object by over-exposing the image.

Further, when the illumination intensity is adjusted based on the brightness of the image detected by the image detecting element, adjustment error can be avoided as the strong reflected light is eliminated from the image, as described above.

The situation eliminating an over-exposure is explained in detail based on a typical example of an arrangement and size of the illumination source, the objective lens and the image detecting element. Similar situations exist, in general, in capsule endoscopes, in which an illumination source and an objective optical system are arranged side-by-side and are covered by a dome-shaped, transparent cover. Therefore the basic idea of the invention can be widely applied to various capsule endoscopes. The illumination means 92 and the imaging means 94 should preferably be arranged as near to each other as possible in order to construct a small-sized capsule endoscope. However, if the image-formation area on the image plane 100 that is symmetrical about the optical axis of the objective optical system 93 to the illumination means 92 is an area used for imaging, an over-exposed object will result for objects touching the periphery of the transparent cover, thereby impeding excellent observation of, for example, the wall of the small intestine. Accordingly, miniaturization of a capsule endoscope is preferably achieved by determining the positional relationship between the illumination means 92 and the image detecting means 94 so that an area that is symmetrically positioned about the optical axis of the objective optical system to the illumination means 92 overlaps an area within the image plane of the image detecting means 94 that is not used for imaging. The area not used for imaging is, for instance, a portion known as 'optical black' that is used for detecting the standard level of optical black in the image plane, and is an area treated with a light shielding mask, and so forth.

In addition, even when an area that is symmetrical about the optical axis to the illumination means is an active image-capturing area of the image detecting means 94, there is no problem so long as the output from this area is ignored during picture image processing (i.e., if this area is 'electrically masked').

As described above, a capsule endoscope is provided which has the ability to obtain an excellent image having no flare or ghosts and also provides a construction that enables miniaturization. Moreover, even when the shape of the transparent cover is not a spherical shape but is an aspheric shape, a capsule endoscope can be provided which has the ability to provide excellent images with little flare and ghosts by determining the positional relationship between the illumination means and the image detecting means so that an area that is symmetrical about the optical axis of the objective optical system to the illumination means overlaps with an area within the image plane of the image detecting element that is not used for image detection, and also by providing a reflection prevention coating on an inside surface of the transparent cover.

Several embodiments of the present invention will now be described with reference to the drawings.

Embodiment 1

Figure 1B:
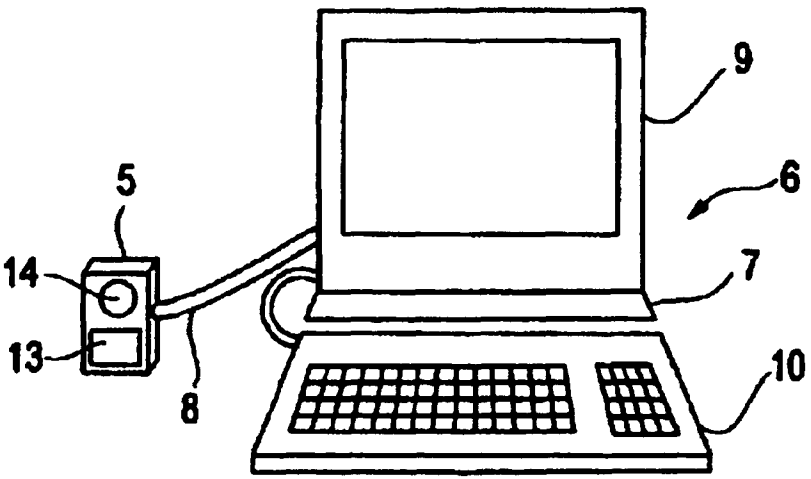
FIGS. 1(A) and 1(B) shows a capsule endoscope system which uses a capsule endoscope according to Embodiment 1 of the present invention.
Figure 1A:
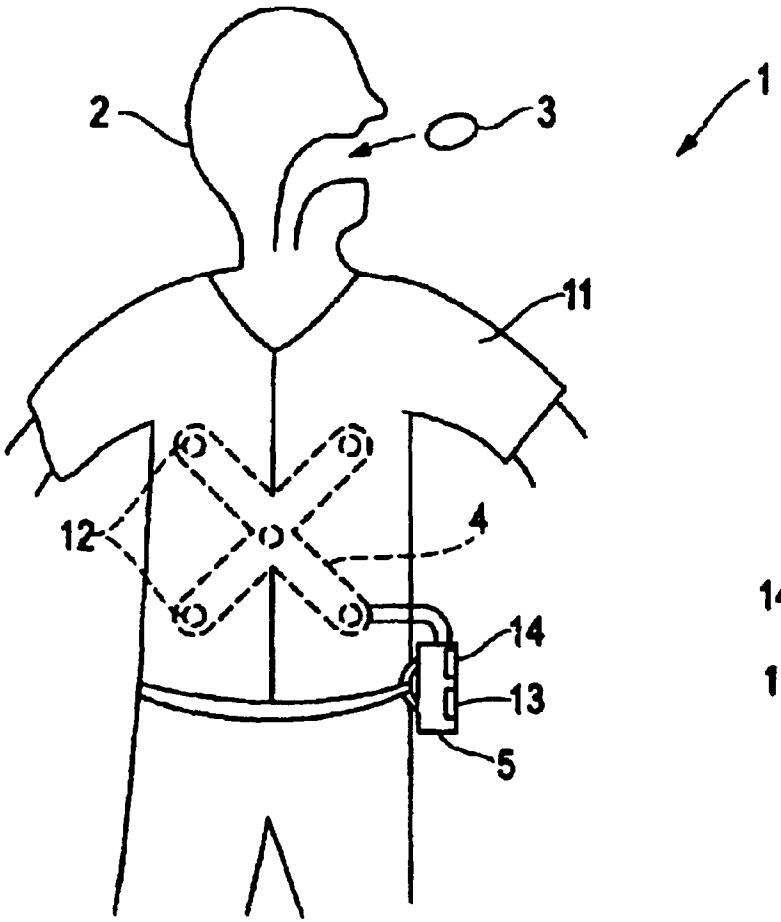
Figure 2A:
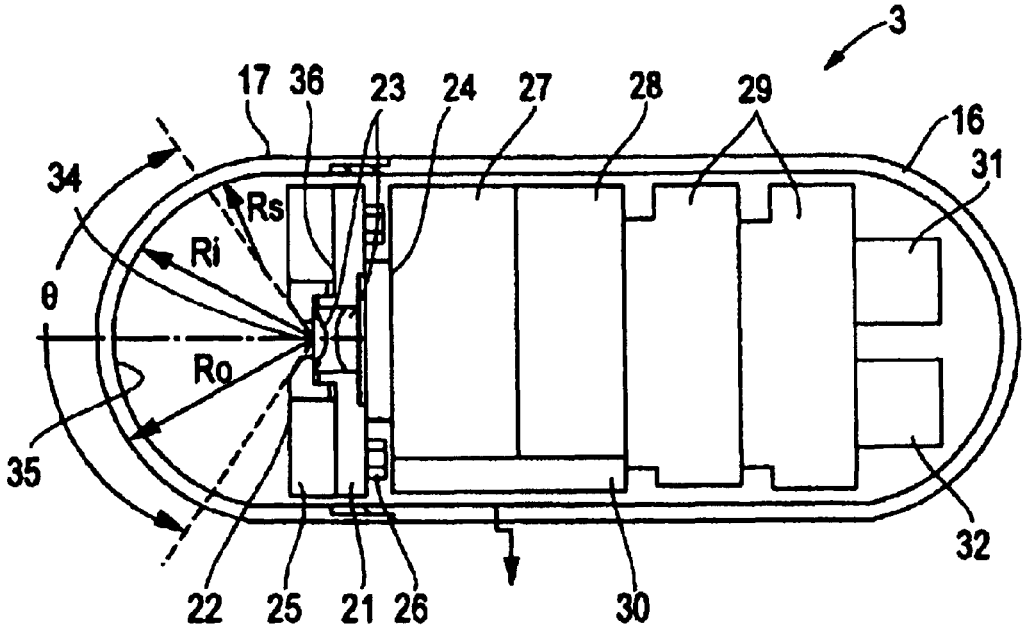
FIG. 2(A) shows a sectional view of the internal structure of a capsule endoscope.
Figure 2B:
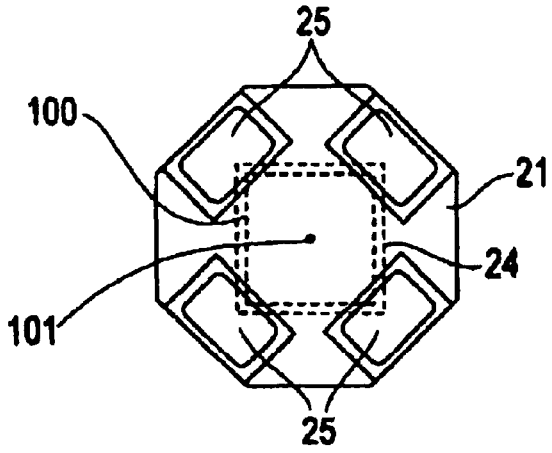
FIG. 2(B) shows the positional relationship between the image detecting means and the illumination means, when viewing the capsule endoscope axially from the object side, according to Embodiment 1 of the invention.
Figure 3:
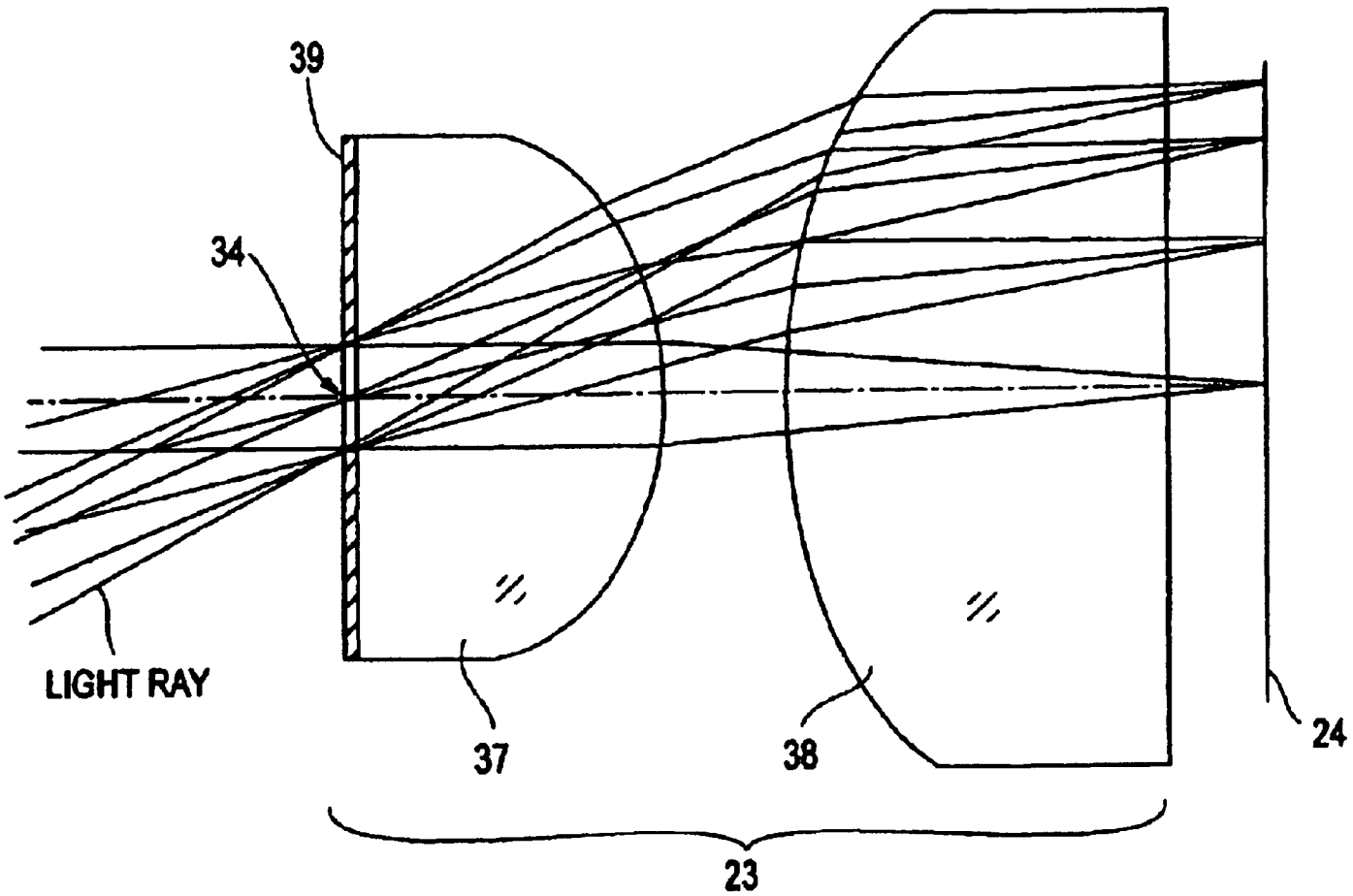
FIG. 3 is an enlarged view of the objective optical system and the image surface of a CMOS image detecting element according to the present invention.
Figure 4A:
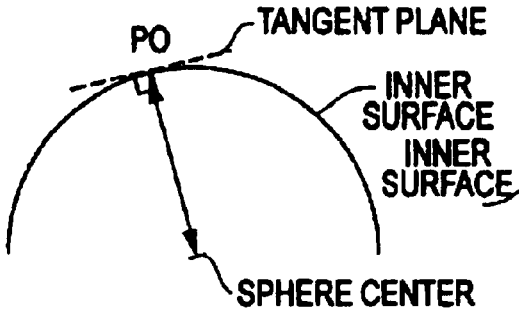
FIGS. 4(A) and 4(B) show the effects of an objective optical system that uses a semi-spherical window, with FIG. 4(A) illustrating the situation of the illuminating light being positioned at the center of curvature of the semi-spherical transparent cover, and with FIG. 4(B) illustrating the situation of the illuminating light being positioned somewhere else.
Figure 4B:
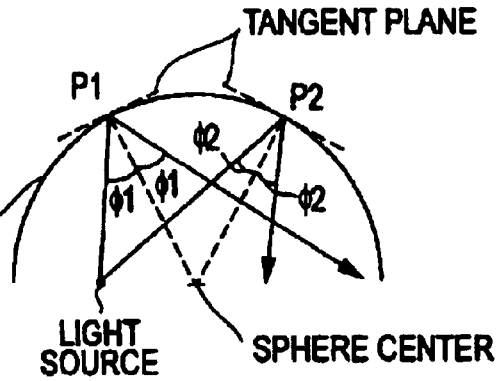

Embodiment 1 will be described with reference to FIGS. 1(A)–4(B). FIGS. 1(A) and 1(B) show a capsule endoscope system which uses a capsule endoscope according to Embodiment 1 of the present invention. FIG. 2(A) is a section view showing the internal structure of the capsule endoscope. FIG. 2(B) is an illustration showing the positional relationship between the image detecting means and the illumination means when viewing the capsule endoscope axially from the object side. FIG. 3 is an enlarged view of the objective optical system. FIGS. 4(A) and 4(B) show the effects of an objective optical system that uses a semi-spherical window, with FIG. 4(A) illustrating the situation of the illuminating light being positioned at the center of curvature of the semi-spherical transparent cover, and with FIG.

4(B) illustrating the situation of the illuminating light being positioned somewhere else.

As shown in FIG. 1(A), a capsule endoscope system 1 uses a capsule endoscope 3 according to Embodiment 1. The capsule endoscope is ingested by the patient 2 through the mouth and passes through the gastrointestinal tract while wirelessly transmitting image data of the inner walls of the gastrointestinal tract. An antenna unit 4 is provided outside the patient's body for receiving image data signals from the capsule endoscope 3, and an external unit 5 is provided for temporarily storing the images. The external unit 5 includes a built-in hard disk of a compact flash memory (R) size having a capacity of, for example, 1 Gigabyte GB in order to store the image data. Image data stored in the external unit 5 can be displayed on a display system 6 (FIG. 1(B)) during or after the examination.

As shown in FIG. 1(B), the external unit 5 is detachably connected to a personal computer 7 that forms the display system 6 via a communication cable such as a USB cable 8. Images stored in the external unit 5 are uploaded onto the personal computer 7, and then saved in its built-in hard disk and/or processed and displayed on a display 9. The personal computer 7 is provided with, for instance, a keyboard 10 for data input.

A USB cable 8 may be provided according to any one of the communication standards USB1.0, USB1.1, or USB2. Other serial data communication types can be used, such as those in accordance with the communication standards RS-232C or IEEE 1384. Moreover, parallel data communication could also be used.

As shown in FIG. 1(A), the patient 2 swallows the capsule endoscope 3 and wears a shielding shirt 11 that includes electrical conductors in a mesh arrangement which provide an electromagnetic shielding effect. The shielding shirt is equipped with an antenna unit 4 that is positioned inside the shielding shirt, (i.e., inside the electrical conductors). The antenna unit 4 receives image data that has been detected and transmitted by the capsule endoscope 3. The image data is stored temporarily in an external unit 5 that is connected to the antenna unit 4. The external unit 5 is held, for instance, on the patient's belt by a detachable hook.

The external unit has, for instance, a box form and carries a liquid crystal monitor 13 for displaying images and an operation button 14 on its front cover for controlling operations. The external unit 5 contains a transmission and reception circuit (i.e., a communication circuit), a control circuit, an image data display circuit, and an electric power source.

As shown in FIG. 2(A), the capsule endoscope 3 is formed of a cylindrical outer cover 16 having a closed, rounded rear end and an open front end to which a semi-spherical, transparent cover 17 is affixed and sealed in a watertight manner.

The sealed capsule contains the following components. An objective optical system 23 with its optical axis aligned with a center axis of the capsule and faces the semi-spherical, transparent cover 17. The objective optical system 23 is fixed to a center barrel of an octagon-shaped circuit board 21 and to a lens frame 22 that is engaged with the center barrel of the circuit board 21. A solid-state image detecting device, such as a CMOS image detecting element 24 is located at the image plane of the objective optical system 23.

As shown in FIG. 2(B), four white LEDs 25 are provided on the front surface of the circuit board 21 around the objective optical system 23. Providing the white LEDs 25 at plural points around the objective optical system 23 as an illumination means enables extensive light delivery in a short distance so as to provide for excellent quality observed images (i.e., captured images).

Further, the miniaturization of a capsule endoscope is devised while maintaining a particular positional relationship between a white LED 25 and a CMOS image detecting element 24 so that areas that are symmetrically situated about the optical axis 101 to the white LEDs 25 (in this case, these areas correspond to the positions of the LEDs 25) overlap an area that is not used for imaging on the image plane 100 of the CMOS image detecting element 24. The white LEDs 25 emit intermittent or flashing light. The image detecting element captures images synchronously with the flashing of the white LEDs 25. This allows low power consumption and excellent observed images having little blurring, even when there is unexpected motion.

As shown in FIGS. 2(A) and 2(B), the circuit board 21 has a square recess on its back surface that accommodates the barrel that supports the objective optical system. The CMOS image detecting element 24 is positioned so that the periphery of its front surface will abut a rear surface of the circuit board 21 near the periphery of the the recess. Chip members 26 that form an LED driving circuit for driving the white LEDs 25 are mounted on the circuit board 21 around the CMOS image detecting element 24. On the backside of the CMOS image detecting element 24, the following components are stacked in the axial direction of the capsule, from front to rear: a driving and processing circuit 27 for driving the CMOS image detecting element 24 and processing image signals from the CMOS image detecting element 24, a wireless communication circuit 28 for performing high frequency modulation of the image signals generated by the driving and processing circuit 27 into wireless transmission signals, and button-shaped batteries 29, 29 for supplying power to the LED driving circuit.

An antenna 30 that is connected to the wireless communication circuit 28 is located adjacent to the driving and processing circuit 27 and to the wireless communication circuit 28. Also, a non-contact-activated switch 31 that can be activated in a non-contact manner and a permanent magnet 32 for guiding the capsule endoscope 3 using magnetic power may be provided, for example, adjacent to the batteries 29, 29 at the rear end of the capsule.

Two contact points with which the non-contact-activated switch 31 is turned on are positioned between one of the electrodes of the serially connected batteries 29, 29 (for instance the positive electrode) and the circuits to which electric power is supplied. Magnetic lines of force having a specified direction may be applied from outside the capsule in order to turn the two contact points to the ON state from the OFF state. When they are turned ON, an internal analogue switch is turned ON and remains in the ON state even when the applied magnetic lines of force are removed. Therefore, the capsule endoscope 3 is able to maintain its operation state when the permanent magnet 32 is magnetized in order to guide the capsule endoscope 3.

The capsule endoscope 3 of this embodiment uses, as shown in FIG. 2(A), a semi-spherical transparent cover 17. The objective optical system 23 is provided within the transparent cover 17 with its entrance pupil 34 located at the center of curvature of the transparent cover 17. More specifically, the transparent cover 17 has inner and outer surfaces having the same center of curvature and with radii of curvature Ri and Ro, for example, equal to 5 mm and 5.5 mm, respectively. Therefore, the thickness of the transparent cover 17 in this embodiment is uniform, making it easy to manufacture.

The objective optical system 23 is installed in the capsule so that its entrance pupil 34 is centered about the same common point, and white LEDs 25 are positioned around the periphery of the objective optical system 23.

The inner surface of the transparent cover 17 has an anti-reflection coating 35 applied thereto, such as transparent dielectric material. This efficiently reduces the amount of light from the illumination means that is undesirably reflected back toward the objective optical system, and thus improves the quality of the detected image data. In order to prevent undesired light from being reflected from the lens frame 22 (and other parts) and entering the objective optical system 23, the front conical surface of the lens frame 22 and the front surface of the circuit board 21 to which the white LEDs are affixed are provided with a light absorbing coating 36. Ideally the light absorbing coating is black in color, but other known light absorbing means can be used, such as other dark-colored coatings, a matte or velvet surface, etc. In this embodiment, the objective optical system 23 is capable of imaging within the visual field angle θ. The front surface of the lens frame has a conical cutout so that incident light within the visual field angle θ can enter the objective optical system 23.

With the above structure, when illumination light from the illumination means is reflected on the inner surface of the transparent cover 17, very little undesired light that has been reflected from components other than the object of interest enters the objective optical system 23.

FIG. 3 is an enlarged view of the objective optical system 23. The objective optical system 23 is formed of, in order from the object side, a first lens 37 that, for example, may be a plano-convex lens element with its planar surface on the object side, and a second lens 38 that, for example, may be a plano-convex lens with its convex surface on the object side. A thin plate or black coating is placed on the front surface of the first lens 37 at the periphery of the entrance pupil position 34 so as to form a brightness stop 39.

The image detecting means (i.e., CMOS image detecting element 24) is positioned behind the second lens 38 with the center of its image detecting area aligned with the optical axis of the second lens 38 of the objective optical system 23. Light proceeding toward the entrance pupil position 34 is contracted by the brightness stop 39 and, as shown in FIG. 3, is imaged on the image plane of the CMOS image detecting element 24.

The operation of this embodiment will now be described. By using a permanent magnet (not shown) which is brought near the rear portion of the capsule endoscope with the lines of force of the magnet having a specified magnetizing direction, the non-contact-activated switch 31 formed of a known, reed-type, switch is turned ON so as to place the capsule endoscope in the operational state.

As will be described in detail, the capsule endoscope 3 then transmits image signals using the antenna 30. Antenna 12 (FIG. 1) receives these image signals and is connected to the external unit 5 which decodes the image signals and displays them on a liquid crystal monitor 13. After confirming that images captured by the capsule endoscope 3 are being displayed on the liquid crystal monitor 13, a patient 2 is allowed to swallow the capsule endoscope 3.

Once swallowed, the capsule endoscope 3 begins its passage through the gastrointestinal tract. When the capsule endoscope 3 is in the operational state, the control part of the driving and processing circuit 27 sends control signals to the LED driving circuit that is formed on the circuit board 21. Then, the LED driving circuit directs the white LEDs 25 to flash at a specific interval.

Light from the white LEDs 25 is transmitted through the transparent cover 17 so as to illuminate regions exterior to the capsule. An illuminated object, such as the esophagus outside the transparent cover 17, is imaged by the objective optical system 23 onto the CMOS image detecting element 24, which is positioned at the image plane of the objective optical system 23. The CMOS image detecting element 24 converts the image to image data in a known manner, depending on the type of image detecting element that is used. Typically, a CMOS image detecting element 24 is used.

Synchronous with the flashing light (for instance, at the end of each flash), the driving and processing circuit 27 sends control signals to the CMOS image detecting element 24 so as to output photoelectric converted signals. The driving and processing circuit 27 performs image processing in which certain signal components are extracted and image signals are generated.

The generated image signals are transferred to the wireless communication circuit 28 and used to modulate a high frequency electromagnetic wave so that the resultant wave can be transmitted via the antenna 30. The electromagnetic wave is received via the antenna unit 4 that is provided outside the body of the patient 2 and demodulated in the external unit 5 (in the reception part of the wireless communication circuit). It is then A/D converted, stored in a hard disk, and processed by the display circuit so as to display the images captured by the CMOS image detecting element 24 on the liquid crystal monitor 13.

When the capsule endoscope 3 approaches the main targeting part, for instance—the small intestine (or when the time comes when the capsule endoscope 3 is expected to approach an object of interest such as the small intestine), the control button 14 of the external unit 5 is used to send a command signal from the external unit 5 to the capsule endoscope 3 which causes the intervals between the flashing of the illumination means and the associated image detecting to shorten. Thus, the image data that is now captured at shorter intervals is temporarily stored on the hard disk of the external unit 5.

When the object is illuminated and imaged in the manner described above, the entrance pupil position 34 of the objective optical system 23 is positioned with its center co-located with the center of the radii of curvature of the surfaces of the semi-spherical transparent cover 17. The white LEDs used as the illumination means are positioned at distant peripheral areas from the sphere center. Therefore, very little illumination light from the illumination means enters the objective optical system 23 even after a portion of this light is reflected from the inner surface of the transparent cover 17. This is illustrated with reference to FIGS. 4(A) and 4(B).

FIG. 4(A) is an illustration showing that light reflected by any point P0 on the inner surface of the transparent cover 17 returns to the sphere center only when it is reflected by a surface having a normal that passes through the point P0. Thus, if the light emitting areas of the white LEDs 25 were to overlap the sphere center, reflected light would return to the sphere center.

FIG. 4(B) is an illustration showing the case in which the sphere center and the light emitting area of a light source do not overlap. In such a case, when light from the light source is reflected by any point P1 or P2 on the inner surface of the transparent cover 17, its angle of reflection is equal to the angle of incidence, as shown (ϕ1 or ϕ2, respectively), and light is not returned to the sphere center.

As shown in FIGS. 4(A) and 4(B), the white LEDs 25 used as the illumination means are located somewhere other than the sphere center of the transparent cover 17. This prevents light reflected by the transparent cover 17 from passing through the sphere center position of the transparent cover 17 or from entering the entrance pupil position 34 of the objective optical system 23. Therefore, flare and ghosting that results from light being reflected on the inner surface of the transparent cover 17 and entering the objective optical system 23 can be effectively prevented.

Further, observations can be performed by overlapping an area within the image plane 100 of a CMOS image detecting element 24, that is not used for image detection, with an area that is symmetrically opposed, about the optical axis of the objective optical system, to a light emitting area of a white LED 25. This embodiment uses a CMOS image detecting element as the solid-state image detecting element (image sensor). However, the type of solid-state image detecting element is not restricted to a CMOS image sensor, and it is apparent that other image sensors, such as CCDs and the following three, more recently developed but known, image sensors can be used. Each has advantages, as described below.

The first image sensor is a next generation image sensor termed a "threshold modulated image sensor (VMIS)" that has the advantages of both CCD and CMOS image detecting elements. Unlike prior art CMOS image detecting elements in which the light receiving part for each pixel consists of three to five transistors and photodiodes, electric charge that is generated by received light modulates the threshold of the MOS transistor. Modulation in the threshold is output as image signals. This type of image sensor is characterized by a combination of high image quality as provided by a CCD image sensor with the higher degree of integration, lower driving voltage, and lower power consumption of a CMOS image sensor. Therefore, a VMIS-type image sensor is particularly well-suited for use in a disposable capsule endoscope. Other beneficial characteristics of a VMIS-type image sensor are: a simple structure that uses only one transistor per image sensor pixel, excellent photoelectric properties such as a high sensitivity and a high dynamic range, and a high density and low price due to the manufacturing techniques being the same as in making a CMOS transistor. Exemplary sensor types include QCIF (QSIF) size, CIF(SIF) size, VGA type, SVGA type, XGA type. Smaller size sensors, such as the QCIF (QSIF) the CIF(SIF) size sensors are especially suitable for the capsule endoscope of the present invention, in terms of the wireless transmission rate, low power consumption, and small size, making the capsule easier to swallow.

The second type of image sensor is termed an 'artificial retina LSI' and is basically a CMOS image sensor that is integrated with an image processing circuit into a chip. This chip simultaneously detects images and performs some image processing, as apparently is similar to the functions performed by the human eye. Conventional CCD and CMOS image sensors only detect images. External image processors are then used to perform characterization and verification processes. The artificial retina chip itself performs these processes. Therefore, the circuit can be simplified and downsized. Further advantages include a high-throughput process, a single power source, and low power consumption. Therefore the 'artificial retina LSI' is suitable for use in disposable capsule endoscopes. Other beneficial characteristics of this type of image sensor include: the ability to conduct image contour extraction, white balance, edge enhancement, brightness adjustment, built-in gamma correction function, and built-in A/D conversion function; high sensitivity and high image quality; a small-sized package; and a built-in noise reduction circuit is available. Exemplary sensor types include QCIF (QSIF) size, 160×144 size, CIF(SIF) size, VGA type, SVGA type, XGA type. Smaller ones such as QCIF (QSIF) size, 160×144 size, and CIF(SIF) size are especially suitable for use in the capsule endoscope of the present invention in terms of wireless transmission rate, low power consumption, and small-size, making the capsule easy to swallow.

The third type of image sensor is a color image sensor having three photo detectors (light receiving layers) arranged in the depth (lengthwise) for each pixel so as to obtain respective RGB color signals, wherein different layers absorb light having different wavelengths. This allows the resolution to be doubled compared to conventional image sensors that use the same number of pixels. This type of image sensor has advantages similar to that of CCDs. The same technology can also be applied to a CMOS image sensor, and the price of such units should become competitive to that of conventional image sensors. The color image sensor uses a VPS (Variable Pixel Size) system that reads several pixels collectively to read respective color signals. This advantageously allows the pixel size to change. This also provides advantages such as high sensitivity for still images and high reading rates required for video images (motion images).

With this type of color image sensor, no false colors are produced. Therefore, it can be used without a low pass filter. This type of color image sensor is suitable for capsule medical devices that require a small size and a low power consumption. It is also suitable for conventional video endoscopes.

The present invention uses wireless transmissions that are conducted according to the BLUETOOTH standard. However, the invention is not restricted to using the BLUETOOTH standard, and a broad band, wireless pulse technique that is currently under development will obviously be applicable to the invention. Broadband has the following advantages: the signal is diffused using a broad band, wireless communication with the signal approaching that of the noise level; therefore, broadband communication can be used in conjunction with a conventional narrow-band communications, and unlike narrow-band communication, carrier frequencies are not used. Therefore, signals can be directly analyzed. For instance, precise distance information is easily retrieved by measuring arrival times. Precise distance information gives one precise location information.

Recently, a pulse wireless communication technology called UWB (Ultra Wide Band) was released and is being commercialized. If incorporated in the wireless communication device of a capsule medical system, the UWB technology allows the use of long wavelengths which are more easily transmitted through the human body. Better transmittance through the human body means that much less power supply is required and, thus, power consumption of the wireless communication device can be reduced. Also with using such a wireless technology, precise position information is also obtained.

Embodiment 2

Figure 5:
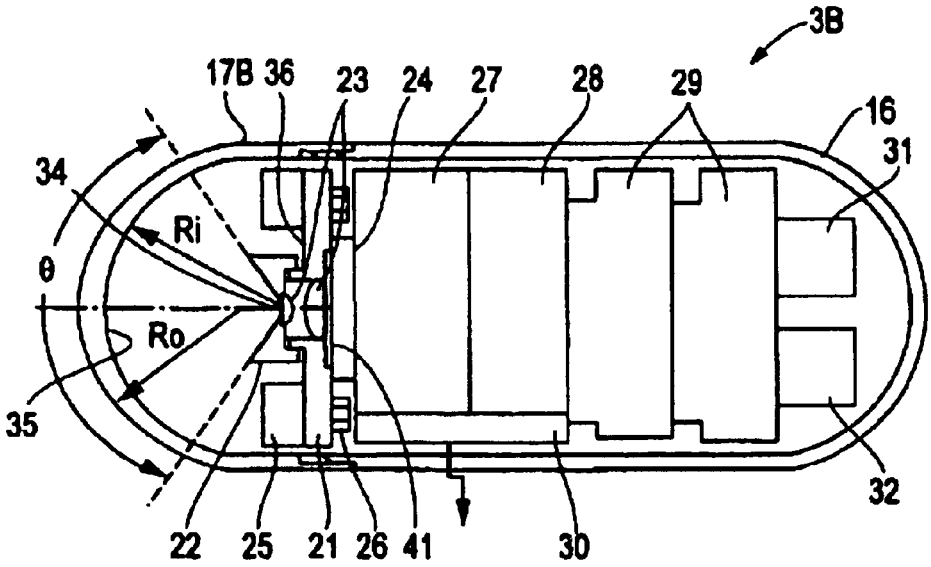
FIG. 5 is a cross-sectional view showing the structure of a capsule endoscope according to Embodiment 2 of the present invention.

Embodiment 2 of the present invention will now be described with reference to FIG. 5. FIG. 5 is a schematic view showing the structure of the capsule endoscope 3B of Embodiment 2. The thickness of the transparent cover 17B in this embodiment is no longer uniform. Instead, the transparent cover 17B is thicker on axis and tapers so as become thinner toward the peripheral regions of the field of view.

The transparent cover 17B is provided with an inner surface having a radius of curvature Ri, for example, equal to 5.5 mm within the visual field angle θ, with the center of curvature coinciding with the center of the entrance pupil 34 of the objective optical system 23.

On the other hand, the outer surface of the transparent cover 17B has a radius of curvature Ro, for example, equal to 5.5 mm within the visual field angle θ. The center of curvature of the outer surface is located on the optical axis but is positioned on the object side of the entrance pupil position 34 of the objective optical system 23. In this case, the distance between the center of curvature of the outer surface and the on-axis position of the entrance pupil is 0.5 mm.

Figure 6:
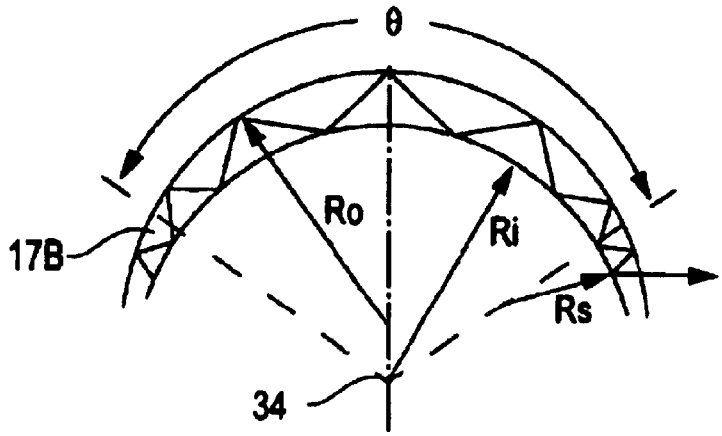
FIG. 6 is an illustration to explain details concerning the operation of the transparent cover.

The inner surface of the transparent cover 17B is composed of two different curved surfaces. One is a spherical surface having a radius of curvature Ri. The other is a doughnut-like surface, with the radius of the doughnut ring being Rs, with Rs<Ri. The centers of these radii are positioned, in cross-section, as illustrated in FIG. 6. Thus, the thickness of the transparent cover reduces from a maximum at the center of the visual field to a minimum at the periphery of the visual field, namely, the contact position of the two different curved surfaces. Due to the small value of Rs (i.e., 3 mm) reduction of the thickness of the cover ceases slightly outside the visual field. Then the cover is connected to the cylindrical portion 17C. When the portion in which the outer radius is Ro and the inner radius is Rs is wide, the thickness reduction of the cover first ceases and then begins to gradually increase. But actually the portion is narrow. Therefore, at a position where the reduction of the thickness almost ceases—this is the portion where the thickness becomes nearly uniform—the cover 17B is connected to the cover 17C. One advantage of using a transparent cover 17B that is thicker in the center, is that the cover is made stronger and is less likely to break, should the capsule be subjected to a mechanical shock. However, there is a second advantage of the transparent cover 17B having a thickness within the visual field angle θ that gradually decreases toward the periphery, in that light reflected by the outside surface of the cover will tend to be guided by being reflected by the inner and outer surfaces until being released at the periphery of the visual field. Thus, undesired light is further prevented from entering the image detecting means, providing excellent observed images. This phenomenon will be explained in greater detail with reference to FIG. 6.

As shown in FIG. 6, a portion of the illumination light from a light source that is transmitted through the inner surface will be reflected by the outer surface of the transparent cover 17B. Part of this light will pass through the inner surface and contribute to stray light that is detected by the image detecting element. Some of the illumination light that is reflected by the outer surface will be totally internally reflected at the inner surface of the transparent cover and will again reach the outer surface of the transparent cover 17B. Moreover, when the transparent cover 17B has a coating such as an anti-reflection coating, the refractive index of the coating should be taken into account. This will not be further discussed, other than to state that a portion of the reflected light from the outer surface of the transparent cover 17B will be repeatedly totally internally reflected between the inner and outer surfaces of the transparent cover. As shown in FIG. 6, the angle of incidence onto the-surfaces decreases with each reflection until such time that the light is no longer totally internally reflected and is released into the air at peripheral areas of the transparent cover 17B. Thus, tapering the thickness of the transparent cover so that it becomes thinner toward the periphery of the visual field angle θ is helpful in reducing stray light that otherwise degrades the images detected by the image detecting means. The radii of curvature of the inner and outer surface within the visual field angle θ can be determined according to the refractive index of the transparent cover 17B so that light that internally reflects within the transparent cover escapes from the transparent cover 17B into the air layer outside the visual field angle θ of the objective optical system 23. This can prevent the adverse effect of flare in the visual field caused by the reflected light from the outer surface of the transparent cover 17B. As described previously, near the periphery of the transparent cover, the curvature of the transparent cover can be increased in a doughnut-shaped region so as to have an apparent radius of curvature, in cross-section, of Rs, where Rs is less than Ro. This enables the length of the transparent cover, and thus of the capsule endoscope itself, to be decreased for a given cylinder diameter of the capsule body.

The objective optical system can serve to correct optical aberrations at the image plane that are caused by the above-discussed tapering in thickness of the transparent cover within the visual field angle θ. Also, in this embodiment, the CMOS image detecting element 24 is covered on its front side by a cover glass 41.

Figure 7:
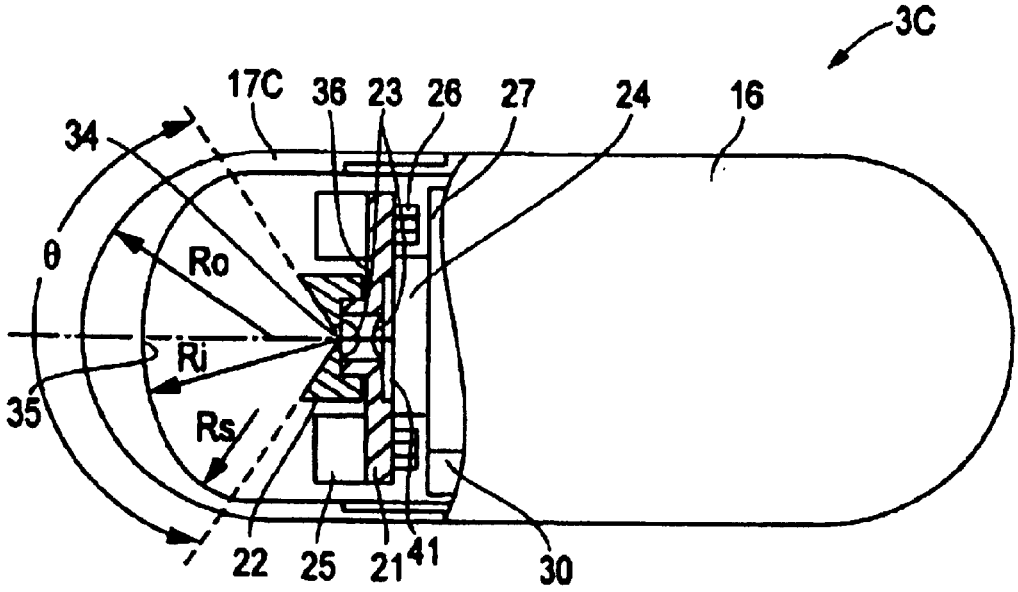
FIG. 7 is a cross-sectional view showing the structure of a capsule endoscope according to a first possible modification to Embodiment 2 of the present invention.

FIG. 7 is an illustration showing the structure of a Modification 1 that can be made to Embodiment 2. The transparent cover in this modification has an outer surface with a radius of curvature Ro equal to, for example, 5.5 mm. This curvature continues nearly to the periphery of the visual field. As before, the center of curvature of the outer surface is located on axis on the object side of the entrance pupil position 34, as illustrated, but in this instance the distance is greater so the transparent cover is thicker on axis. As before, the transparent cover has an inner surface that is a combination of a spherical surface and a doughnut-shaped surface. The spherical portion of the inner surface covers the central region of the visual field and extends almost to the periphery of the visual field. It has a radius of curvature Ri of, for example, 6 mm, and the center of curvature of the spherical region of the inner surface is on-axis at the entrance pupil position of the objective optical system. The doughnut-shaped portion of the inner surface begins near the periphery of the visual field. As before, the center of the doughnut is on axis and is positioned on the object side of the entrance pupil position 34, with the radius of curvature of the ring of the doughnut being Rs, as illustrated in cross-section in FIG. 7. As before, Rs<Ri, and the thickness of the transparent cover decreases from a maximum at the center of the visual field toward the periphery. Due to the small value of Rs (i.e., 3 mm) reduction of the thickness of the cover ceases slightly outside the visual field. The transparent cover portion 17C is then engaged with the leading edge of the outer cover 16 and sealed in a watertight manner.

Modification 1 effectively prevents the illumination light from the white LEDs 25 from entering the objective optical system 23 even if it is reflected by the inner surface of the transparent cover 17C. In addition, by having the thicker center part, the transparent cover 17C is made more sturdy and is better able to withstand mechanical shocks.

Figure 8:
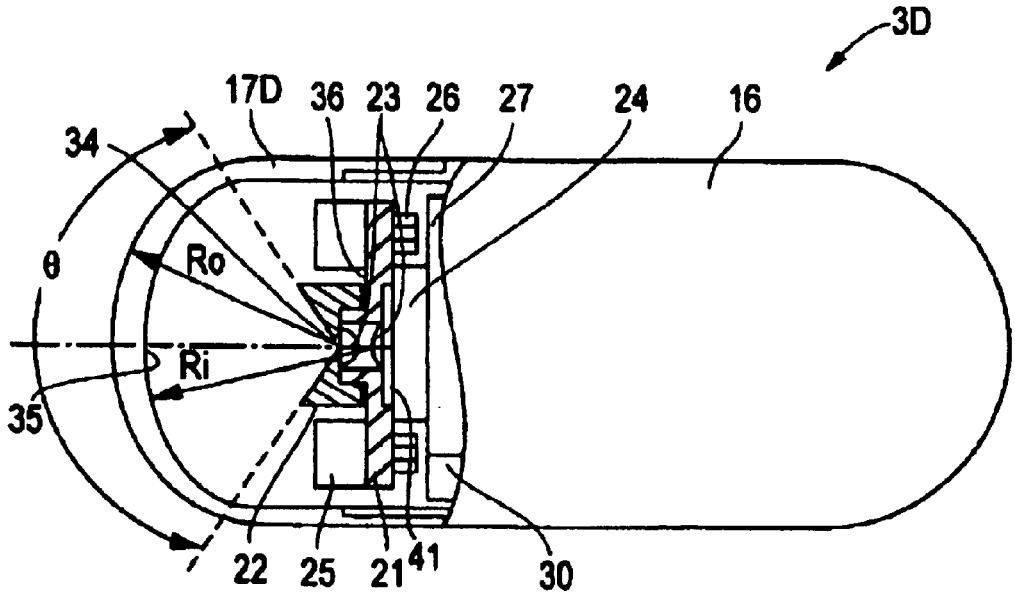
FIG. 8 is a cross-sectional view showing the structure of a capsule endoscope according to a second possible modification to Embodiment 2 of the present invention.
Figure 9:
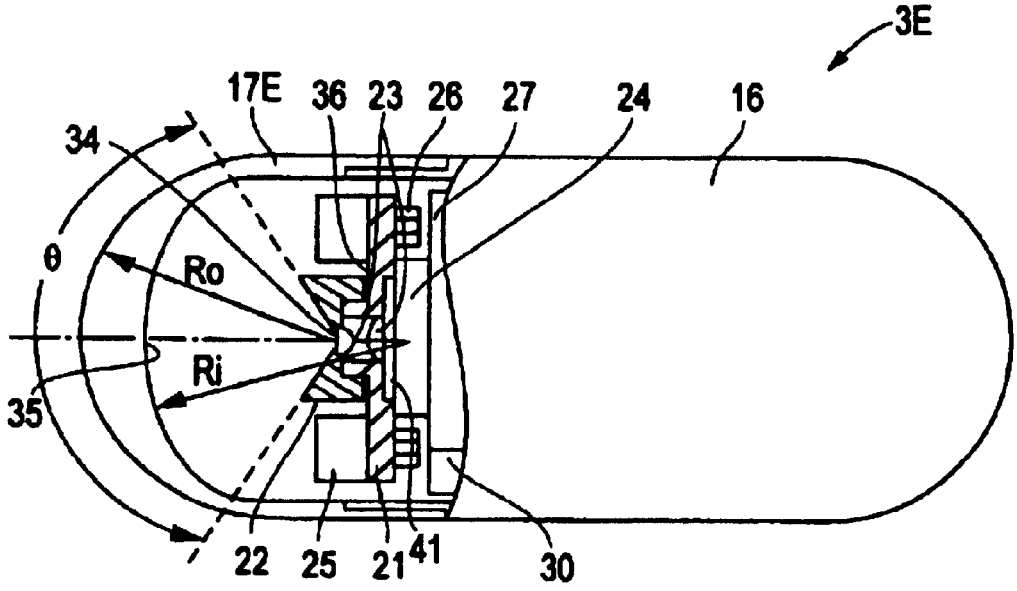
FIG. 9 is a cross-sectional view showing the structure of a capsule endoscope according to a third possible modification to Embodiment 2 of the present invention.

FIGS. 8 and 9 show the structures of the capsule endoscopes 3D and 3E of Modifications 2 and 3, respectively, to this embodiment. In the capsule endoscopes 3D and 3E, the transparent covers 17D and 17E, respectively, have an outer surface with a radius of curvature Ro (for example, Ro=5.5 mm) and the center of curvature of the outer surface coincides with the axial position of the entrance pupil position 34. The centers of curvature of the inner surfaces of the transparent covers 17D and 17E lie to the image-side of the axial positions of the entrance pupil positions 34, 34. For example, the transparent cover 17D has an inner surface radius of curvature Ri of 5.5 mm and the transparent cover 17E has an inner surface radius of curvature Ri of 6 mm. Modifications 2 and 3 use an anti-reflection coating 35 to effectively prevent the illumination light from the white LEDs 25 from being reflected by the inner surface of the transparent cover 17D or 17E.

Embodiment 3

Figure 10A:
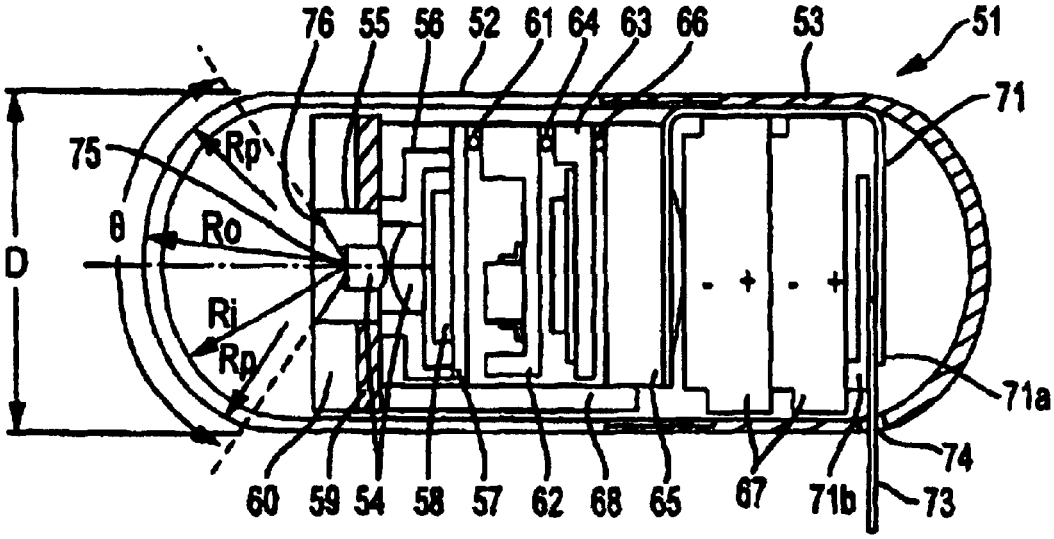
FIGS. 10(A) and 10(B) relate to Embodiment 3 of the present invention, with FIG. 10(A) being a cross-sectional view, and FIG. 10(B) showing the positional relationship between the illumination means and the image detecting element when viewing the capsule endoscope axially from the object side.
Figure 10B:
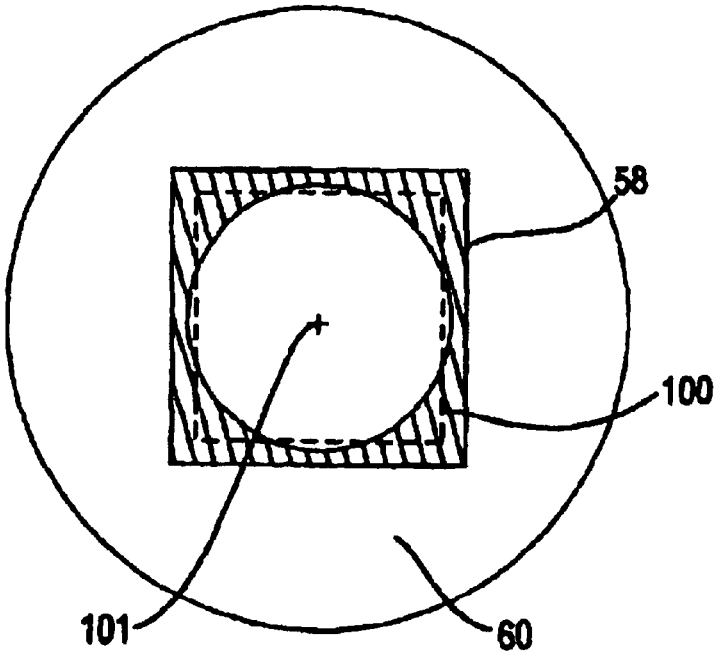

FIG. 10(A) is a cross-sectional view of an capsule endoscope 51 of Embodiment 3 of the present invention. FIG. 10(B) is an illustration showing the positional relationship between the illumination means and the image detecting element when viewing the capsule endoscope axially from the object side. Referring to FIG. 10(A), the capsule endoscope 51 includes a transparent front cover 52 that has a cylinder form with a semi-spherical front end and a rear cover 53 which also is shaped as a cylinder that has a semi-spherical rear end. The rear end of the transparent front cover 52 and the front end of the rear cover are fitted to each other and sealed so as to create a watertight capsule container in which an objective optical system 54 and other elements are housed.

The objective optical system 54 is formed of a first lens supported by a first lens frame 55 and a second lens supported by a second lens frame 56, and is positioned along the axis of symmetry of the capsule with its entrance pupil 75 facing the front cover 52. A CMOS image detecting element 58 is affixed onto the front surface of a circuit board 57 and is positioned at the image surface formed by the objective optical system 54. White LEDs 60 are provided on a circuit board 59 which is engaged with, and fixed to, the second lens frame 56. As shown in FIG. 10(B), a white LED 60 that is ring-shaped is centered about the optical axis 101 of an objective optical system. A portion of the ring-shaped, white LED 60 overlaps an area (shown with cross-hatching in FIG. 10(B)) of the image plane 100 of a CMOS image detecting element 58 that is not used for image detection. The circuit board 57, on which the CMOS image detecting element 58 is mounted, is electrically connected via a connector 61 to a circuit board onto which other electronic elements are mounted so as to form a driving and processing circuit 62. A circuit board that includes a memory circuit 63 and other electronic components is positioned behind and connected, via a connector 64 to the circuit board on which the driving and processing circuit 62 is mounted. A circuit board that supports a wireless communication circuit 65 is positioned behind and connected via a connector 66 to the circuit board that Supports the memory circuit 63. Two button-shaped batteries 67 are positioned behind the circuit board that supports the wireless communication circuit 65.

An antenna 68 is positioned adjacent to the circuit board that supports the driving and processing circuit 62. For instance, a negative electrode of the serially connected batteries 67, 67 is connected to the ground of the wireless communication circuit 65 and to the ground of the other circuits via a lead (not labeled). The positive terminal of the wireless communication circuit 65 and the positive terminals of the other circuits are connected to one end of a spring contact member 71. The spring contact member 71 includes a contact part 71a positioned behind the serially connected batteries 67, 67. An insulating plate 73 is detachably positioned between the contact part 71a of the spring contact member 71 and the contact part 71b that contacts the positive electrode of the batteries. Thus, because the insulating plate 73 prevents electrical contact between the contact part 71a and the contact part 71b, the OFF state of the capsule endoscope is established.

Part of the insulating plate 73 extends through the capsule endoscope wall via a small cut-out part which has a rubber valve part 74. By pulling out the insulating plate 73, the spring-biased contact part 71a is allowed to contact the contact part 71b so as to establish the ON state. The rubber valve part 74 automatically seals closed so as to maintain a watertight condition once the insulating plate 73 is pulled out from the capsule endoscope. The transparent dome part of the front cover 52 has inner and outer surfaces with constant radii of curvature Ri and Ro, respectively, that extend nearly to the periphery of the visual field θ. In this embodiment, Ri is 6.0 mm and Ro is 6.5 mm. The centers of curvature of both the inner and outer surfaces of the dome coincide with the axial position of the entrance pupil 75 of the objective optical system 54. Thus, this embodiment uses a transparent dome having a uniform thickness within the central part of the visual field θ. Near the periphery of the visual field θ, the outer surface of the transparent dome has a radius of curvature Rp that is smaller than either of the radii of curvature Ri and Ro (for instance Rp=4.0 mm) so that the outer surface continues until it meets the cylindrical body of the capsule. The capsule endoscope 51 of this embodiment has an outer body diameter D of 11 mm. The first lens frame 55 has a conical front surface 76 that is roughened so as to diffuse light that is incident thereon. Due to the arrangement of the components and the design of the transparent cover, this embodiment, also effectively prevents a portion of the illumination light that is reflected from the inner and outer surfaces of the front cover 52 from entering the objective optical system 54. In other words, it effectively prevents undesired light from entering the objective optical system 54, thereby achieving excellent quality images.

Embodiment 4

Figure 11B:
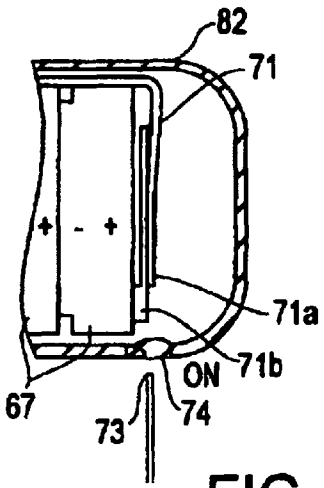
FIGS. 11(A)–11(D) relate to Embodiment 4 of the present invention, with FIG. 11(A) being a cross-sectional view, with FIG. 11(B) showing the ON state, with FIG. 11(C) showing the positional relationship between the illumination means and the image detecting element when viewing the capsule endoscope axially from the object side, and with FIG. 11(D) showing a possible modification to the positional relationship shown in FIG. 11(C)
Figure 11A:
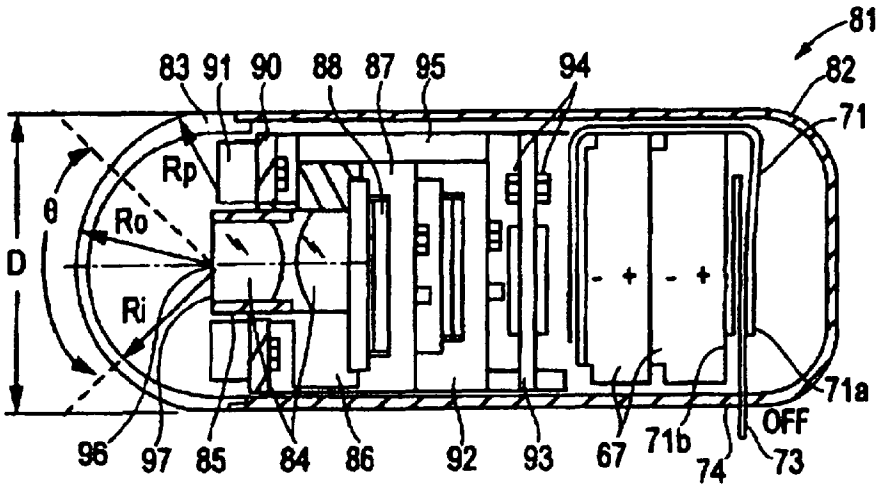
Figure 11D:
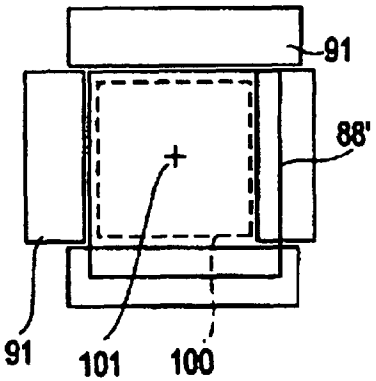
Figure 11C:
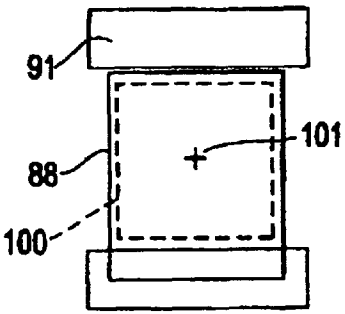

FIG. 11(A) shows, in cross-section, the structure of the capsule endoscope 81 of Embodiment 4 of the present invention. FIG. 11(B) shows the ON state of the capsule endoscope of this embodiment. FIG. 11(C) shows the positional relationship between the illumination means and the image detecting element when viewing the capsule endoscope axially from the object side, and FIG. 11(D) shows a possible modification to the positional relationship shown in FIG. 11(C).

The capsule endoscope 81 of this embodiment includes a cylindrical outer cover 82 having a closed, rounded rear end and a front end with which a nearly semi-spherical transparent cover 83 is engaged and sealed to create a watertight structure in which an objective optical system 84 and other elements are housed. The objective optical system 84 is formed of, in order from the object side, a first lens that is supported by a first lens frame 85 and a second lens that is supported by a second lens frame 86. A CCD 88, that is positioned within a recess provided on the front surface of a circuit board 87, is positioned with its detecting surface at the image plane of the objective optical system 84. White LEDs 91 are attached to a circuit board 90 that is fixed to the barrel of the second lens frame 86 which engages with the first lens frame 85.

As shown in FIG. 11(C), the white LED 91 is arranged so that, as viewed from the front of the capsule, the area on the image detecting surface that is symmetrically opposed about the optical axis 101 to the white LED 91 is not used for image detection. However, this area may be an active area of the CCD that is used for detecting 'optical black'. The optical black portion is an area where the picture elements are shielded by masking (physically or electrically) the image detecting surface 100 and thus is an area not used for image detection. In addition, as shown in FIG. 11(D), two white LEDs 91 may be used with an image detecting element. In this instance a different type CCD 88' is used. The CCD 88' comprises an optical black component (that portion of CCD 88' which is shown with diagonal lines and is not used for image detection) and a signal reading component. Accordingly, the white LEDs 91 are arranged so that areas (namely, the areas shown by the diagonal lines in FIG. 11(D) that are symmetrically opposed about the optical axis 101 of the objective optical system to the LEDs 91 overlap with an area of the image detecting element that is not used for imaging. FIGS. 11(C) and 11(D) have been simplified for purposes of explanation by showing fewer LED's 91 than may actually exist.

Behind the circuit board 87 on which the CCD 88 is mounted, a circuit board 92 is positioned on which electronic components are mounted that form a driving, processing and memory circuit. Behind the circuit board 92 there is a circuit board which Supports a wireless communication circuit 93. Electronic chip elements 94, 94 and components of the wireless communications circuit 93 are mounted on both sides of the circuit board. Button-shaped batteries 67 are provided behind the circuit board that supports the wireless communications circuit 93. An antenna 95 is positioned adjacent to the circuit boards 87 and 92.

As shown in FIGS. 11(A) and 11(B), the serially connected batteries 67,67 have their positive electrode in electrical contact with a contact part 71b. As previously described with regard to FIG. 10(A), spring contact member 71a, is prevented from contacting contact part 71b by an insulating plate 73 that is positioned between these members, so that the OFF state is established. By pulling out the insulating plate 73, the contact parts 71a and 71b are allowed to contact each other so as to establish the ON state.

This embodiment uses a transparent cover 83 having, within the visual field θ, inner and outer surfaces with radii of curvature Ri and Ro equal to 4.5 mm and 5.0 mm, respectively. Both the inner and outer surfaces of the transparent cover 83 have a common center of curvature that is positioned at the axial position of the entrance pupil 96 of the objective optical system 84. Thus, within the visual field θ in this embodiment, the transparent cover 83 has a uniform thickness of 0.5 mm. Outside the visual field θ the curvature of the transparent cover outer and inner surfaces is different (with the outer surface having an apparent radius of curvature, as seen in cross-section, of Rp) so that the transparent cover fits smoothly to a capsule endoscope body having an outer diameter of 11 mm. Such a design enables the overall capsule length to be shortened. Furthermore as noted above, the front end of the transparent cover has a smaller radius of curvature than one-half the value of the outer diameter of the capsule endoscope 81. This contributes to a reduced overall length of the capsule endoscope 81. Also, this embodiment uses a cylindrical first lens frame 85. The first lens, fixed within the first lens frame 85, has a front surface that is provided with a thin plate or a coating for shielding light around the entrance pupil position 96 so as to form a brightness stop 97.

One feature of this embodiment is that the position of engagement of the transparent cover to the capsule can be adjusted lengthwise before sealing so that the entrance pupil position 96 of the objective optical system 84 coincides with the center position of the radii of curvature Ri and Ro of the transparent cover 83. In other words, the portion of the transparent cover 83 that engages with the cylindrical outer cover 82 can be used as a positioning means to locate the entrance pupil position 96 of the objective optical system 84 at the center of curvature, within the visual field θ. Providing a positioning means ensures precise positioning of the entrance pupil position 96 of the objective optical system 84 at the center position of the radii of curvature Ri and Ro of the transparent cover 83. The positioning adjustment can be conducted using an optical adjusting apparatus (not illustrated). Also, the positioning can be conducted by operating the capsule endoscope and positioning the transparent cover to a position where flare light is minimized. The structure for positioning that is disclosed in other embodiments is also applicable to this embodiment.

Embodiment 5

Figure 12A:
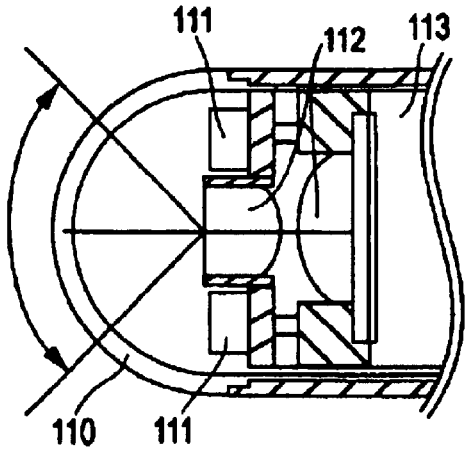
FIGS. 12(A)–12(C) relate to Embodiment 5 of the present invention, with FIG. 12(A) being a cross-sectional view of the tip portion of the capsule endoscope, with FIG. 12(B) showing the positional relationship between the illumination means and the image detecting element when viewing the capsule endoscope axially from the object side, and with FIG. 12(C) showing a first possible modification to the positional relationship shown in FIG. 12(B)
Figure 12B:
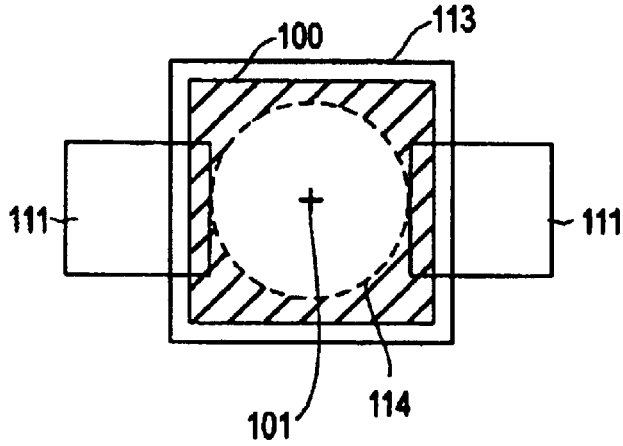
Figure 12C:
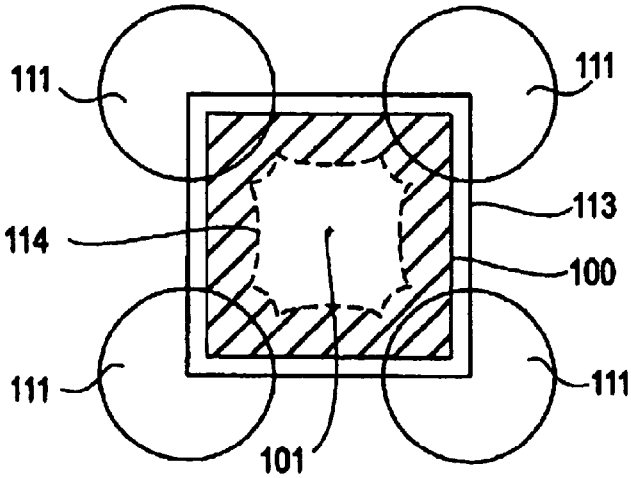

FIG. 12(A) is a cross-sectional view of the tip portion of the capsule endoscope according to Embodiment 5 of the present invention. FIG. 12(B) illustrates the positional relationship between the image detecting means and the illumination means when viewing the capsule endoscope axially from the object side. FIG. 12(C) is an illustration showing the positional relationship between the image detecting means and the illumination means when viewing the capsule endoscope axially from the object side in a modified example of Embodiment 5.

In a capsule endoscope according to the present embodiment, the transparent cover 110 has its outer and inner surfaces semi-spherical in shape with a common center of curvature, and the objective optical system 112 is arranged inside the capsule so that the center of its entrance pupil coincides with the common center of curvature of the transparent cover 110, as shown in FIG. 12(A). The image detecting surface 100 (FIG. 12(B)) of a CCD 113 is arranged at the image plane of the objective optical system 112. Four white LEDs 111 are attached at the periphery of the objective optical system 112. Further, as shown in FIG. 12(B), miniaturization of the capsule endoscope is achieved by determining the positional relationship between the white LEDs and the CCD 113 so that a peripheral area 114 (shown by cross-hatching in FIG. 12(B)) of the CCD that is electrically masked so as to not provide image signals from these areas is symmetrically opposed to the white LEDs 111 about the optical axis 101. This electrical masking is illustrated as if an actual physical mask were placed on the image plane 100, but, in fact, it is implemented by ignoring, for image-formation purposes, image pixel data in the areas indicated.

The electrically-implemented mask 114 in this embodiment has the effect of there being a round shape that is projected onto the image plane 100, since distortion aberration of the objective optical system 112 is corrected. An area inside the electrically-implemented mask 114 is the area used for imaging.

A first modified example of Embodiment 5 is shown in FIG. 12(C). In FIG. 12(C), the electrically-implemented mask 114 is a more complex shape, in order to account for the objective optical system 112 generating negative distortion. In this modified example, four white LEDs 111, which form the illumination means for this embodiment, are arranged with their centers near the four corners of the CCD 113. The four white LEDs 111 are positioned relative to the CCD 113, as viewed axially from the front of the capsule endoscope, so that an area that is symmetrically positioned about the optical axis of the objective optical system from a light emitting area of the illumination means overlaps an area of the CCD 113 but does not overlap any area of the CCD 113 that is used for picture imaging. By arranging the LEDs as above and electrically masking the area as indicated to account for negative distortion created by the objective optical system 112, a small-scale capsule endoscope can be provided that has the ability to observe images while avoiding over-exposure. This is accomplished by masking (electrically or otherwise) those pixel elements which otherwise would be over-exposed by the detected light containing a high proportion of specularly reflected light. This specularly reflected light arises both from light that is reflected at the transparent cover inner and outer surfaces, and from light that is reflected from lumen wall surfaces, especially lumen wall surfaces that contact the peripheral portions of the transparent cover.

Figure 13A:
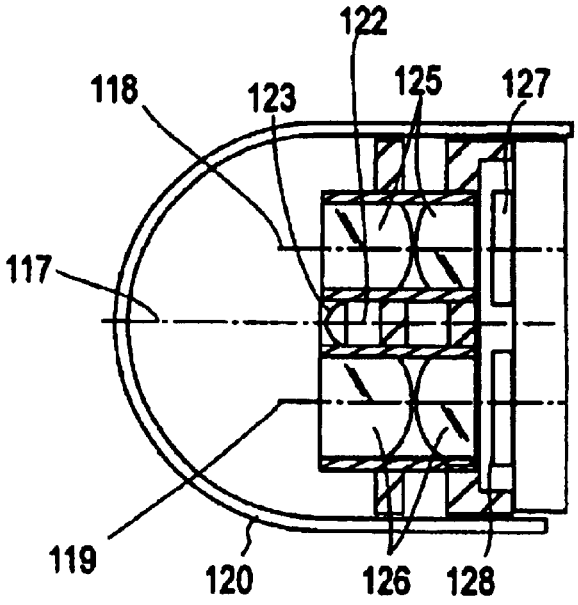
FIGS. 13(A) and 13(B) relate to a second possible modification to Embodiment 5 wherein, instead of using a single lens for imaging, left and right imaging systems that are capable of providing images having different parallax for 3-D viewing are positioned within the capsule, with FIG. 13(A) being a cross-sectional view showing a construction of the main components of the tip portion of a capsule endoscope that includes a plurality of objective optical systems, and with FIG. 13(B) showing the positional relationship between the imaging means and the illumination means when viewing the capsule endoscope axially from the object side.
Figure 13B:
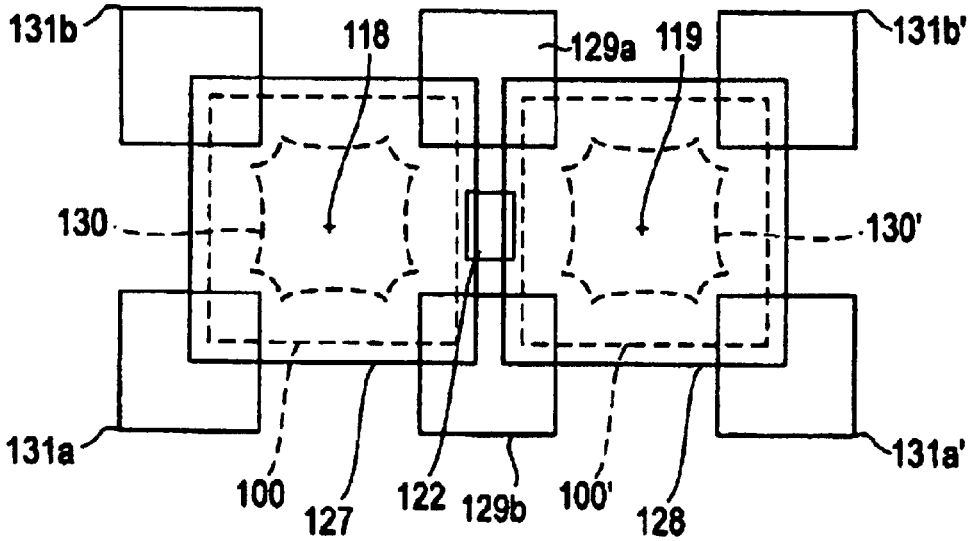

A second modified example of Embodiment 5 is shown in FIGS. 13(A) and 13(B). As shown in FIG. 13(A), a capsule endoscope having left and right objective optical systems for capturing images having parallax is provided, so that images for 3-D displays can be captured by the capsule endoscope. In this modified example of Embodiment 5, the exit pupil of an illumination means is placed at the center of curvature of the transparent cover, and left and right objective optical systems are used on either side of the illumination means.

The capsule endoscope according to this modification to Embodiment 5 employs a transparent cover 120 having a front portion that is semi-spherical in shape, as shown in FIG. 13(A). An output pupil of a light diffusion means 123 is arranged in front of a white LED 122 which is placed along the central axis of the cylindrical-shaped center portion of the capsule body. The center of the output pupil of the light diffusion means 123 is preferably placed so as to coincide with the center of curvature of the inner and outer surfaces of the transparent cover 120. The objective optical systems 125 and 126 are arranged on opposite sides of the white LED 122, and the image detecting surfaces (FIG. 13(B)) of CCDs 127 and 128 are arranged at the image planes 100 and 100' of respective objective optical systems 125 and 126. In addition, white LEDs 129a and 129b (not illustrated in FIG. 13(A)) may be positioned as indicated in FIG. 13(B), where a line segment connecting the centers of the LEDs 129a and 129b intersect, a line segment connecting the centers of the image detecting elements 118 and 119, and the central axis 117 of the diffusion means intersect at a common point.

Further, as shown in FIG. 13(B), peripheral areas outside the dotted lines labeled 130 and 130' that include portions of regions of 131a, 131a', 131b, 131b' that are symmetrically positioned about the optical axis of each objective optical system from light emitting areas of illumination means (namely, the non-centered LEDs 129a and 129b), as well as regions which take into account the negative distortion of the objective optical systems 125 and 126, are electrically masked so that they do not contribute to the image detected by the image detecting elements 127 and 128.

By electrically masking selected areas of the image detecting elements 127 and 128 in this manner, even in a capsule endoscope having a plurality of image detecting elements and a plurality of illumination means, it is possible to obtain properly exposed images containing parallax of a viewed object by, in effect, ignoring those pixel areas of the image detecting elements of the image sensors that will be over-exposed as a result of either the transparent cover or an object of interest specularly reflecting a proportion of the illumination light into the image sensor via the objective optical systems.

Figure 14A:
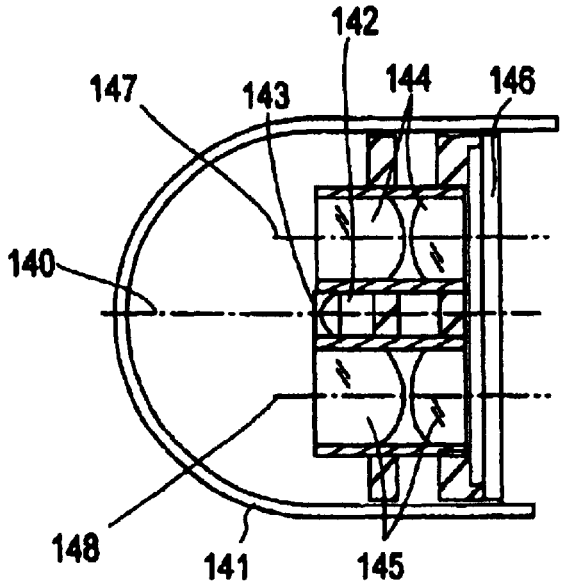
FIGS. 14(A) and 14(B) relate to a third possible modification to Embodiment 5, with FIG. 14(A) showing a cross-sectional view of the construction of the main components of the tip portion of a capsule endoscope comprising a plurality of objective optical systems, and with FIG. 14(B) showing the positional relationship between the imaging means and the illumination means when viewing the capsule endoscope axially from the object side.
Figure 14B:
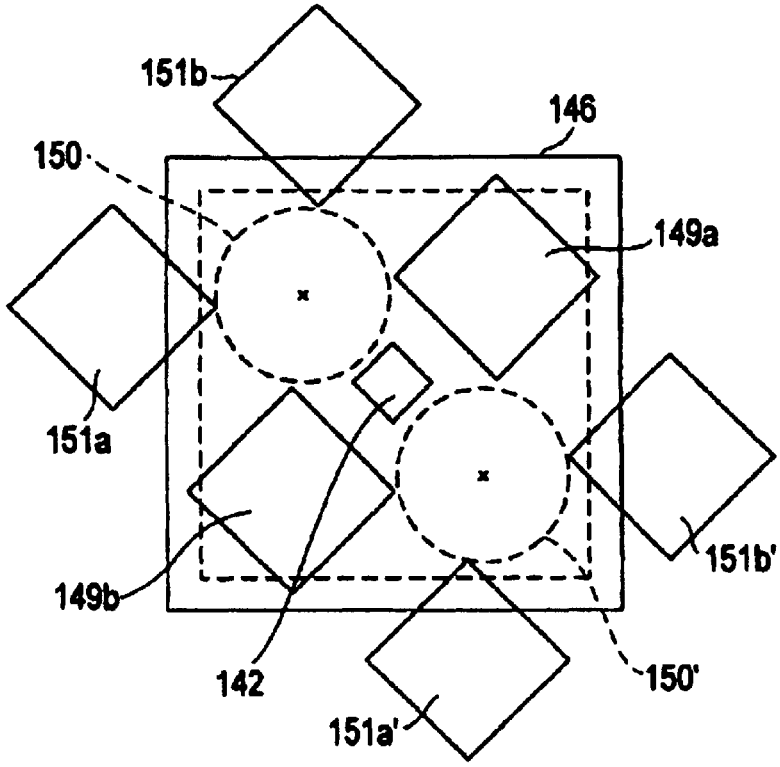

FIGS. 14(A) and 14(B) relate to a third possible modification to Embodiment 5, with FIG. 14(A) being a cross-sectional view of the construction of the main components of the tip portion of a capsule endoscope comprising a plurality of objective optical systems, and with FIG. 14(B) showing the positional relationship between the illumination means and the imaging means when viewing the capsule endoscope axially from the object side. Once again, an output pupil of a light diffusion means 143 is arranged in front of a white LED 142 which is placed along the central axis 140 of the cylindrical-shaped center portion of the capsule endoscope body. The center of the output pupil of the light diffusion means 143 is preferably placed so as to coincide with the center of curvature of the inner and outer surfaces of the transparent cover 141. The objective optical systems 144 and 145 are arranged on opposite sides of the white LED 142, and the image plane of a shared CCD 146 is positioned to be co-planar with the image planes of the objective optical systems 144 and 145. In addition, white LEDs 149a and 149b (not illustrated in FIG. 14(A) but shown in FIG. 14(B)) may be positioned as indicated (i.e., symmetrically about the LED 142, as viewed from the front of the capsule).

Further, as shown in FIG. 14(B), peripheral areas outside the dotted lines labeled 150 and 150' that include portions of regions 151a, 151a', 151b, 151b' that are symmetrically positioned about the optical axis of each objective optical system from light emitting areas of illumination means (namely, the non-centered LEDs 149a and 149b), as well as regions which take into account the negative distortion of the objective optical systems 144 and 145, are electrically masked so that they do not contribute to the images detected by the shared image detecting element 146.

By electrically masking selected areas of the image detecting element 146 in this manner, even in a capsule endoscope having a plurality of illumination means, it is possible to obtain properly exposed images containing parallax of a viewed object by, in effect, ignoring those pixel areas of the image detecting element that will be over-exposed as a result of light being specularly reflected by the transparent cover surfaces or a lumen wall that is in contact at a peripheral region of the transparent cover into the image detecting element via the objective optical systems.

In all of the embodiments, the anti-reflection coating on the inner surface of tile transparent cover is advantageous in reducing undesired light that would otherwise indirectly enter the objective optical system via the inner surface of the transparent cover from outside the visual field, as well as in reducing undesired light that enters the visual field directly. In addition, a water repellant coating on the outer surface of the transparent cover prevents contaminants from adhering to the transparent cover, thereby obstructing observations.

Of course, it is essential that the transparent cover and the capsule endoscope body are made of materials that are not harmful to humans. Further, it is important that all of the components of the capsule endoscope do not harm the environment when disposed of in a low cost manner. In this way, a capsule endoscope that is disposable after each use may be provided at a reasonably low cost.

The invention being thus described, it will be obvious that the same may be varied in many ways. For example, combinations of the features described in the preferred embodiments may be selectively used. Rather, the scope of the invention shall be defined as set forth in the following claims and their legal equivalents. All such modifications as would be obvious to one skilled in the art are intended to be included within the scope of the following claims.

What is claimed is:

1. A capsule endoscope, comprising:

illumination means that includes a light emitting element for illuminating an object;

imaging means for imaging the object; and a transparent cover having a center of curvature, said transparent cover covering the illumination means and the imaging means;

wherein the imaging means includes an objective optical system and an image detecting element;

an entrance pupil position of the objective optical system is arranged so that its center is located substantially at the center of curvature of the transparent cover; and the illumination means is positioned relative to the image detecting element, when viewing the capsule endoscope from the object side, so that an area that is symmetrically positioned about the optical axis of the objective optical system from a light emitting area of the illumination means overlaps an area of the image detecting element but does not overlap any area of the image detecting element that is used for picture image detection.

2. The capsule endoscope according to claim 1, wherein an area of the image detecting element that is not used for picture imaging and which is symmetrically positioned, when viewing the capsule endoscope from the object side, about the optical axis of the objective optical system from a light emitting area of the illumination means is a mask area that is treated electrically at the time of the picture image processing.

3. The capsule endoscope according to claim 1, wherein the transparent cover has an inner surface and an outer surface, the center of curvature of the inner surface being located substantially at the entrance pupil position; and the transparent cover has a thickness that, from a maximum opposite the entrance pupil, decreases toward the periphery of the transparent cover.

4. A capsule endoscope, comprising:

illumination means that includes a light emitting element for illuminating an object;

imaging means that includes an objective optical system for imaging the object; and a transparent cover having a center of curvature, said transparent cover covering the illumination means and the imaging means;

wherein the illumination means includes an illumination diverging means having an exit pupil, and a light emitting element, and the center of the exit pupil of the illumination diverging means is arranged to substantially coincide with the center of curvature of the transparent cover.

5. The capsule endoscope according to claim 4, wherein the imaging means comprises a plurality of lens elements that constitute the objective optical system, and an image detecting element.

6. A capsule endoscope, comprising:

illumination means for illuminating an object;

imaging means for imaging the object; and a transparent cover having a center of curvature, said transparent cover covering the illumination means and the imaging means;

wherein the imaging means includes a plurality of objective optical systems and an image detecting element;

the illumination means include illumination diverging means having exit pupils and light emitting elements;

one exit pupil of the illumination diverging means is arranged so as to substantially coincide with the center of curvature of the transparent cover, and the remaining exit pupils of the illumination diverging means are positioned relative to the image detecting element, when viewing the capsule endoscope from the object side, so that areas that are symmetrically positioned about the optical axes of the objective optical systems from the exit pupils of the remaining illumination diverging means overlap areas of the image detecting element but do not overlap any area of the image detecting element that is used for picture image detection.

7. The capsule endoscope according to claim 6, wherein an area of the image detecting element that is not used for picture imaging and which is symmetrically positioned, when viewing the capsule endoscope from the object side, about the optical axes of the objective optical system from a light emitting area of the illumination means is a mask area that is electrically masked at the time of the picture image processing.

8. A capsule endoscope, comprising:

illumination means for illuminating an object;

imaging means for imaging the object; and a transparent cover having a center of curvature, said transparent cover covering the illumination means and the imaging means;

wherein the imaging means includes a plurality of objective optical systems and a plurality of image detecting elements;

the illumination means include illumination diverging means having exit pupils, and light emitting elements;

the exit pupil of one illumination diverging means is arranged to substantially coincide with the center of curvature of the transparent cover, and the exit pupils of the remaining illumination diverging means are positioned relative to the image detecting elements, when viewing the capsule endoscope from the object side, so that areas that are symmetrically positioned about the optical axes of the objective optical systems from the exit pupils of the remaining illumination diverging means overlap areas of the image detecting elements but do not overlap any area of the image detecting elements that is used for picture image detection.

9. A capsule endoscope, comprising:

illumination means that includes a light emitting element for illuminating an object;

imaging means for imaging the object; and a transparent cover which covers the illumination means and the imaging means;

wherein the imaging means includes an objective optical system and an image detecting element, the illumination means is positioned relative to the image detecting element, when viewing the capsule endoscope from the object side, so that an area that is symmetrically positioned about the optical axis of the objective optical system from a light emitting area of the illumination means overlaps an area of the image detecting element but does not overlap any area of the image detecting element that is used for picture image detection.

10. The capsule endoscope according to claim 9, wherein an area of the image detecting element that is not used for picture imaging and which is symmetrically positioned, when viewing the capsule endoscope from the object side, about an optical axis of the objective optical system from a light emitting area of the illumination means is a mask area that is electrically masked at the time of the picture image processing.

11. The capsule endoscope according to claim 9, wherein:

the objective optical system has an entrance pupil;

the transparent cover has an outer surface, the center of curvature of the outer surface being located substantially at the entrance pupil position; and the transparent cover has a thickness that, from a maximum opposite the entrance pupil, decreases toward the periphery of the transparent cover.

*12. A capsule endoscope, comprising:*

*illumination means that includes a light emitting element for illuminating an object;*

*imaging means for imaging the object; and*

*a transparent cover having a center of curvature, said transparent cover covering the illumination means and the imaging means;*

*wherein*

*the imaging means includes an objective optical system and an image detecting element;*

*an entrance pupil position of the objective optical system is arranged so that its center is located substantially at the center of curvature of the transparent cover; and*

*the illumination means is positioned off of the center of curvature, whereby light from the illumination means which is internally reflected by the transparent cover does not pass through the center of curvature and does not enter the entrance pupil position of the objective optical system.*

*13. The capsule endoscope according to claim 12, wherein the illumination means includes a plurality of light emitting elements which are arranged around the center of curvature, near the periphery of the transparent cover.*

*14. The capsule endoscope according to claim 12, wherein the transparent cover has a semi-spherical shape with a uniform thickness.*

*15. The capsule endoscope according to claim 14, wherein the entrance pupil position is arranged so that it is located substantially at the center of curvature, within a specified visual field, of both an inner surface and an outer surface of the transparent cover.*

*16. The capsule endoscope according to claim 12, wherein the transparent cover has a semi-spherical shape.*

*17. The capsule endoscope according to claim 16, wherein the thickness of the transparent cover is thicker on the optical axis of the objective optical system and tapers so as to become thinner toward the peripheral regions of the field of view.*

*18. The capsule endoscope according to claim 12, wherein the illumination means comprises an even number of LEDs arranged around the periphery of the objective optical system.*

*19. A capsule endoscope, comprising:*

*illumination means that includes a light emitting element for illuminating an object;*

*imaging means for imaging the object; and*

*a transparent cover having a center of curvature, said transparent cover covering the illumination means and the imaging means;*

*wherein*

*the imaging means includes an objective optical system and an image detecting element;*

*an entrance pupil position of the objective optical system is arranged so that its center is located substantially at the center of curvature of the transparent cover; and*

*the illumination means is positioned somewhere else than the center of curvature, whereby light from the illumination means that is reflected by the inner surface of the transparent cover is not returned to the center of curvature and does not enter the entrance pupil position of the objective optical system.*

*20. The capsule endoscope according to claim 19, wherein the illumination means includes a plurality of light emitting elements which are arranged around the center of curvature, near the periphery of the transparent cover.*

*21. The capsule endoscope according to claim 19, wherein the transparent cover has a semi-spherical shape with a uniform thickness.*

*22. The capsule endoscope according to claim 19, wherein the entrance pupil position is arranged so that its center is located, within a specified visual field, substantially at the center of curvature of the inner surface of the transparent cover.*

*23. The capsule endoscope according to claim 22, wherein the transparent cover has a semi-spherical shape.*

* * * * *